US005998499A

United States Patent [19]
Klee et al.

[11] Patent Number: 5,998,499
[45] Date of Patent: Dec. 7, 1999

[54] LIQUID CRYSTALLINE (METH)ACRYLATE COMPOUNDS, COMPOSITION AND METHOD

[75] Inventors: Joachim E. Klee, Radolfzell; Holger Frey, Freiburg; Dirk Holter, Lörrach; Rolf Mulhaupt, Freiburg, all of Germany

[73] Assignee: Dentsply G.m.b.H., Germany

[21] Appl. No.: 08/723,443

[22] Filed: Oct. 7, 1996

Related U.S. Application Data

[63] Continuation-in-part of application No. 08/543,950, Oct. 17, 1995, abandoned, and a continuation-in-part of application No. 08/217,998, Mar. 25, 1994, Pat. No. 5,624,976, and a continuation-in-part of application No. 08/231,535, Apr. 22, 1994, abandoned.

[51] Int. Cl.$^6$ .................................................. A61K 6/083
[52] U.S. Cl. ......................... 523/118; 523/115; 523/116; 524/559; 526/326; 560/138; 560/221; 433/228.1; 252/299.61; 252/299.66
[58] Field of Search ..................................... 523/115, 116, 523/118; 524/559; 526/326; 560/138, 221; 433/228.1

[56] References Cited

U.S. PATENT DOCUMENTS

| | | |
|---|---|---|
| 150,262 | 4/1874 | Slavin . |
| 173,850 | 2/1876 | Emde . |
| D. 195,391 | 6/1963 | Pakison ........................... D81/1 |
| 212,975 | 4/1879 | Perkins et al. . |
| D. 315,956 | 4/1991 | Dragan ........................... D24/14 |
| D. 353,673 | 12/1994 | Discko, Jr. et al. ............. D24/152 |
| 543,829 | 7/1895 | Gurnee . |
| 3,066,112 | 11/1962 | Bowen ........................... 260/1 |
| 3,150,801 | 9/1964 | Hamilton ....................... 222/158 |
| 3,200,142 | 8/1965 | Bowen ........................... 260/286 |
| 3,256,226 | 6/1966 | Fekete ........................... 260/23.5 |
| 3,317,469 | 5/1967 | Feichtinger et al. ............ 260/47 |
| 3,327,016 | 6/1967 | Lee ................................. 260/830 |
| 3,327,017 | 6/1967 | Huang et al. ................... 260/844 |
| 3,466,259 | 9/1969 | Jernigan ......................... 260/37 |
| 3,503,128 | 3/1970 | Boyd et al. ..................... 32/15 |
| 3,539,533 | 11/1970 | Lee, II et al. .................. 260/17 |
| 3,564,074 | 2/1971 | Swisher et al. ................ 260/837 |
| 3,586,527 | 6/1971 | Aronoff et al. ................ 117/93.31 |
| 3,595,969 | 7/1971 | Shepherd et al. .............. 260/28.5 |
| 3,634,542 | 1/1972 | Dowd et al. ................... 260/837 |

(List continued on next page.)

FOREIGN PATENT DOCUMENTS

| | | |
|---|---|---|
| 563464 | 9/1958 | Canada . |
| 817442 | 7/1969 | Canada . |

(List continued on next page.)

OTHER PUBLICATIONS

Lal et al; Journal of Polymer Science: vol. XXIV, pp. 75–84 (1957) New Polymerization Catalysts for Methyl Methacrylate.

Beaunez et al: Journal of Polymer Science: Part A: Polymer Chemistry, vol. 32, pp. 1459–1469 (1994).

Antonucci et al; Journal of Dental Research 58(9), pp. 1887–1899, Sep. 1979; New Initiator Systems for Dental Resins based on Ascorbic Acid.

Chemistry Abstrat 115 (1991) 78952z and Chemistry Abstract 115 (1991) 78973g.

Klee et al, Polymer Bulletin 27 (1992); pp. 511–517.

Chemical Abstract, vol. 89, No. 18, Oct. 30, 1978, Columbis OH, US; Abstract No. 148211C; p. 71, Column 2; abstract & Lakokras Mater. IKH, Primen., No. 4, 1978, pp. 50–52.

Dusek et al; American Chemical Society (1984) Transesterification and Gelation of Polyhydroxy Esters Formed from Diepoxides and Dicarboxylic Acids.

Hartel et al; (Nov. 1984) Zur Synthese linearer Additionspolymere aus Diandiglycidether und Dicarbonsauren.

Klee; Acta Polymer 44, 163–167 (1993); Synthesis and investigation of β,w–methacryloyl poly (epoxide–carboxylic acid and β,w–methacryloyl poly (epoxide–phenol)–macromonomers.

J. Klee et al, Acta Polymer 42 (1991) 17–20.

Fukushima et al; Dental Materials Journal 4(1): pp. 33–39 (1985): Application of Functional Monomers for Dental Use (Part 9) Sysntheses of Succinoxy Methacrylates and Their Adhesion to Polished and Etched Tooth Surfaces.

Lin et al; Journal of Polymer Science; Part A: Polymer Chemistry, vol. 30, 1941–1951 (1992).

Allard et al; Journal of Polymer Science: Polymer Chemistry Edition, vol. 22, 3827–3842 (1984).

Hage et al; American Chemical Society (1986) Poly(acrylourethane)–Polyepoxide Semi–interpenetrating Networks Formed by Electron–Beam Curing.

Dubuisson et al; Rheol. Acta 20, 463–470 (1981).

Klee; Acta Polymer., 45, 73–82 (1994) Telechelic prepolymers and macromonomers by step growth processes.

John Wiley & Sons; Encyclopedia of Polymer Science and Engineering, vol. 8, Identification to Lignin (1987).

Litt et al; J. Polymer Science, Part A: Polymer Chemistry; "Crosslinked Liquid Crystal Polymers from Liquid Crystal Monomers: Synthesis and Mechanical Properties" vol. 31, No. 1, pp. 183–191; 1993.

Holter et al, Macromolecules (MAMOBX, 00249297); "Liquid Crystalline Themosets Based on Branched Bismethacrylates"; vol. 29 (22); pp. 7003–7011 (1996).

*Primary Examiner*—Andrew E. C. Merriam
*Attorney, Agent, or Firm*—Dale R. Lovercheck; James B. Bieber

[57] ABSTRACT

A liquid crystalline compound, a polymeric product formed by polymerization of the liquid crystalline compound, a dental composition including the liquid crystalline compound and method of using the dental composition. Polymerization of the liquid crystalline compound results in an low volume percent shrinkage and a high conversion to polymer. The composition of the invention is useful for dental adhesive, primer, cement, pit and fissure sealant and restorative.

37 Claims, 1 Drawing Sheet

U.S. PATENT DOCUMENTS

| | | | |
|---|---|---|---|
| 3,673,558 | 6/1972 | Toepel et al. | 260/29.2 |
| 3,709,866 | 1/1973 | Waller | 260/27 |
| 3,742,949 | 7/1973 | Hill | 128/218 |
| 3,754,054 | 8/1973 | Khnura et al. | 260/860 |
| 3,769,336 | 10/1973 | Lee, Jr. et al. | 260/486 |
| 3,815,239 | 6/1974 | Lee, Jr. et al. | 32/15 |
| 3,835,090 | 9/1974 | Gander et al. | 260/42.15 |
| 3,845,009 | 10/1974 | Gander | 260/42.15 |
| 3,853,962 | 12/1974 | Gander | 260/486 |
| 3,882,187 | 5/1975 | Takiyama et al. | 260/835 |
| 3,889,385 | 6/1975 | Dougherty | 32/12 |
| 3,926,906 | 12/1975 | Lee, II et al. | 260/42.53 |
| 3,971,765 | 7/1976 | Green et al. | 260/78 |
| 3,973,972 | 8/1976 | Muller | 106/39.7 |
| 3,980,483 | 9/1976 | Nishikubo et al. | 96/115 |
| 4,002,669 | 1/1977 | Gross et al. | 260/486 |
| 4,051,195 | 9/1977 | McWhorter | 260/837 |
| 4,081,492 | 3/1978 | Traenckner et al. | 260/837 |
| 4,097,569 | 6/1978 | Waters | 264/255 |
| 4,097,994 | 7/1978 | Reaville et al. | 32/15 |
| 4,098,735 | 7/1978 | Tobias | 260/18 |
| 4,100,045 | 7/1978 | Bogan et al. | 204/159.16 |
| 4,135,868 | 1/1979 | Schainholz | 422/310 |
| 4,141,865 | 2/1979 | Bogan | 260/18 |
| 4,150,012 | 4/1979 | Joos | 260/42.15 |
| 4,177,563 | 12/1979 | Schmitz-Josten et al. | 433/228 |
| 4,182,035 | 1/1980 | Yamauchi et al. | 433/228 |
| 4,182,833 | 1/1980 | Hicks | 528/120 |
| 4,197,390 | 4/1980 | Jackson | 528/115 |
| 4,220,582 | 9/1980 | Orlowski et al. | 260/42.28 |
| 4,229,376 | 10/1980 | Rogier | 260/563 P |
| 4,253,830 | 3/1981 | Kazen et al. | 433/77 |
| 4,255,468 | 3/1981 | Olson | 427/137 |
| 4,256,457 | 3/1981 | Behring | 433/77 |
| 4,284,742 | 8/1981 | Bowerman, Jr. et al. | 525/329 |
| 4,293,074 | 10/1981 | Dunsky | 206/572 |
| 4,296,004 | 10/1981 | Rogier | 260/18 EP |
| 4,308,085 | 12/1981 | Horhold et al. | 156/330 |
| 4,362,889 | 12/1982 | Bowen | 560/221 |
| 4,383,826 | 5/1983 | Butler et al. | 433/228 |
| 4,383,879 | 5/1983 | Le Du et al. | 156/307 |
| 4,384,853 | 5/1983 | Welsh | 433/90 |
| 4,391,590 | 7/1983 | Dougherty | 433/90 |
| 4,405,766 | 9/1983 | Bertram et al. | 525/507 |
| 4,406,625 | 9/1983 | Orlowski et al. | 433/228 |
| 4,413,105 | 11/1983 | Koenig | 525/482 |
| 4,431,421 | 2/1984 | Kawahara et al. | 433/228 |
| 4,446,246 | 5/1984 | McGinniss | 502/155 |
| 4,467,079 | 8/1984 | Hechenberger et al. | 526/90 |
| 4,514,342 | 4/1985 | Billington et al. | 260/952 |
| 4,515,634 | 5/1985 | Wu et al. | 106/35 |
| 4,524,161 | 6/1985 | Feuerhahn | 523/414 |
| 4,541,992 | 9/1985 | Jerge et al. | 422/300 |
| 4,547,531 | 10/1985 | Waknine | 523/116 |
| 4,548,689 | 10/1985 | Sakashita et al. | 204/159.23 |
| 4,557,848 | 12/1985 | Sung et al. | 252/51.5 |
| 4,569,662 | 2/1986 | Dragan | 433/89 |
| 4,579,904 | 4/1986 | Orlowski et al. | 524/554 |
| 4,595,734 | 6/1986 | O'Hearn | 525/524 |
| 4,643,303 | 2/1987 | Arp et al. | 206/370 |
| 4,714,751 | 12/1987 | Schornick et al. | 528/103 |
| 4,758,643 | 7/1988 | Tanaka et al. | 526/279 |
| 4,767,326 | 8/1988 | Bennett et al. | 433/90 |
| 4,774,063 | 9/1988 | Runnells | 422/297 |
| 4,781,921 | 11/1988 | Smith et al. | 424/81 |
| 4,789,620 | 12/1988 | Sasaki et al. | 430/280 |
| 4,806,381 | 2/1989 | Engelbrecht et al. | 427/2 |
| 4,816,495 | 3/1989 | Blackwell et al. | 522/14 |
| 4,816,528 | 3/1989 | Dervan et al. | 525/438 |
| 4,854,475 | 8/1989 | Riihimaki et al. | 220/337 |
| 4,863,993 | 9/1989 | Montgomery | 524/854 |
| 4,866,146 | 9/1989 | Janda et al. | 526/213 |
| 4,872,936 | 10/1989 | Engelbrecht | 156/307.3 |
| 4,874,799 | 10/1989 | Hung et al. | 522/96 |
| 4,883,899 | 11/1989 | Muramoto et al. | 560/14 |
| 4,918,136 | 4/1990 | Kawaguchi et al. | 524/751 |
| 4,931,096 | 6/1990 | Fujisawa et al. | 106/35 |
| 4,936,775 | 6/1990 | Bennett | 433/220 |
| 4,950,697 | 8/1990 | Chang et al. | 523/116 |
| 4,959,199 | 9/1990 | Brewer | 422/300 |
| 4,963,093 | 10/1990 | Dragan | 433/90 |
| 4,964,911 | 10/1990 | Ibsen et al. | 106/35 |
| 4,969,816 | 11/1990 | Drumm | 433/90 |
| 4,985,198 | 1/1991 | Hirasawa et al. | 560/130 |
| 4,985,516 | 1/1991 | Sakashita et al. | 526/196 |
| 5,006,066 | 4/1991 | Rouse | 433/77 |
| 5,052,927 | 10/1991 | Discko, Jr. | 433/90 |
| 5,083,921 | 1/1992 | Dragan | 433/90 |
| 5,100,320 | 3/1992 | Martin et al. | 433/90 |
| 5,106,301 | 4/1992 | Miyhara et al. | 433/214 |
| 5,108,287 | 4/1992 | Yee et al. | 433/77 |
| 5,122,057 | 6/1992 | Discko, Jr. | 433/90 |
| 5,129,825 | 7/1992 | Discko, Jr. | 433/90 |
| 5,137,990 | 8/1992 | Corley | 525/530 |
| 5,151,479 | 9/1992 | Mukai et al. | 526/277 |
| 5,165,890 | 11/1992 | Discko, Jr. | 433/90 |
| 5,166,117 | 11/1992 | Imai et al. | 502/169 |
| 5,172,810 | 12/1992 | Brewer | 206/369 |
| 5,173,273 | 12/1992 | Brewer | 422/300 |
| 5,189,077 | 2/1993 | Kerby | 523/116 |
| 5,204,398 | 4/1993 | Cohen et al. | 524/403 |
| 5,210,157 | 5/1993 | Schutyser et al. | 525/502 |
| 5,215,726 | 6/1993 | Kudla et al. | 422/300 |
| 5,217,372 | 6/1993 | Truocchio | 433/215 |
| 5,235,008 | 8/1993 | Hefner, Jr. et al. | 525/529 |
| 5,236,362 | 8/1993 | Cohen et al. | 433/228.1 |
| 5,252,629 | 10/1993 | Imai et al. | 523/118 |
| 5,267,859 | 12/1993 | Discko, Jr. | 433/89 |
| 5,279,800 | 1/1994 | Berr, Jr. | 422/300 |
| 5,284,632 | 2/1994 | Kudla et al. | 422/297 |
| 5,294,413 | 3/1994 | Riikimaki et al. | 422/297 |
| 5,322,440 | 6/1994 | Steele | 433/90 |
| 5,324,273 | 6/1994 | Discko, Jr. | 604/240 |
| 5,340,551 | 8/1994 | Berry, Jr. | 422/300 |
| 5,346,677 | 9/1994 | Risk | 422/297 |
| 5,360,877 | 11/1994 | Hwang et al. | 525/423 |
| 5,384,103 | 1/1995 | Miller | 422/310 |
| 5,567,349 | 10/1996 | Kelly et al. | 252/299.01 |

FOREIGN PATENT DOCUMENTS

| | | |
|---|---|---|
| 1107751 | 8/1971 | Canada . |
| 878004 | 8/1971 | Canada . |
| 878006 | 8/1971 | Canada . |
| 966500 | 4/1975 | Canada . |
| 983491 | 2/1976 | Canada . |
| 987044 | 4/1976 | Canada . |
| 995667 | 8/1976 | Canada . |
| 1018294 | 9/1977 | Canada . |
| 1030979 | 5/1978 | Canada . |
| 1099848 | 4/1981 | Canada . |
| 1100990 | 5/1981 | Canada . |
| 1107293 | 8/1981 | Canada . |
| 1115289 | 12/1981 | Canada . |
| 1131827 | 9/1982 | Canada . |
| 1140939 | 2/1983 | Canada . |
| 1151667 | 8/1983 | Canada . |
| 1153391 | 9/1983 | Canada . |
| 1155141 | 10/1983 | Canada . |
| 1175196 | 9/1984 | Canada . |
| 1183144 | 2/1985 | Canada . |
| 1185982 | 4/1985 | Canada . |
| 1189996 | 7/1985 | Canada . |

| | | | | | | |
|---|---|---|---|---|---|---|
| 1200555 | 2/1986 | Canada . | | 227 363 | 1/1984 | Czech Rep. . |
| 1202749 | 4/1986 | Canada . | | 037 759 | 10/1981 | European Pat. Off. . |
| 1210777 | 9/1986 | Canada . | | 120 559 | 1/1983 | European Pat. Off. . |
| 1219990 | 3/1987 | Canada . | | 104 491 | 4/1984 | European Pat. Off. . |
| 1227202 | 9/1987 | Canada . | | 115 410 | 4/1984 | European Pat. Off. . |
| 1235423 | 4/1988 | Canada . | | 115 948 | 8/1984 | European Pat. Off. . |
| 1242213 | 9/1988 | Canada . | | 188 752 | 12/1984 | European Pat. Off. . |
| 1248126 | 1/1989 | Canada . | | 212 193 | 3/1987 | European Pat. Off. . |
| 1258465 | 8/1989 | Canada . | | 219 058 | 4/1987 | European Pat. Off. . |
| 2019410 | 2/1990 | Canada . | | 277 413 | 10/1988 | European Pat. Off. . |
| 2002017 | 5/1990 | Canada . | | 356 868 | 3/1990 | European Pat. Off. . |
| 1270846 | 6/1990 | Canada . | | 0 379 058 | 7/1990 | European Pat. Off. . |
| 2005912 | 6/1990 | Canada . | | 0 675 186 | 10/1995 | European Pat. Off. . |
| 2006431 | 6/1990 | Canada . | | 1 003 448 | 8/1958 | Germany . |
| 2006432 | 6/1990 | Canada . | | 2 126 419 | 12/1971 | Germany . |
| 2006433 | 6/1990 | Canada . | | 141 667 | 5/1980 | Germany . |
| 2006434 | 6/1990 | Canada . | | 154 945 | 6/1982 | Germany . |
| 2004624 | 7/1990 | Canada . | | 209 358 | 4/1984 | Germany . |
| 2026009 | 7/1990 | Canada . | | 208 365 | 5/1984 | Germany . |
| 1272735 | 8/1990 | Canada . | | 214 381 | 10/1984 | Germany . |
| 2008895 | 8/1990 | Canada . | | 229 140 | 10/1985 | Germany . |
| 2009471 | 8/1990 | Canada . | | 244 748 | 4/1987 | Germany . |
| 2012824 | 9/1990 | Canada . | | 35 36 076 | 4/1987 | Germany . |
| 2014027 | 10/1990 | Canada . | | 35 36 077 | 4/1987 | Germany . |
| 2014359 | 10/1990 | Canada . | | 248 598 | 8/1987 | Germany . |
| 1276168 | 11/1990 | Canada . | | 261 365 | 10/1988 | Germany . |
| 1276648 | 11/1990 | Canada . | | 277 078 | 3/1990 | Germany . |
| 1277070 | 11/1990 | Canada . | | 277 689 | 4/1990 | Germany . |
| 2054747 | 11/1990 | Canada . | | 279 667 | 8/1990 | Germany . |
| 2010210 | 12/1990 | Canada . | | 295 758 | 11/1991 | Germany . |
| 2018728 | 12/1990 | Canada . | | 41 41 174 | 6/1992 | Germany . |
| 2054710 | 12/1990 | Canada . | | 41 09 048 | 9/1992 | Germany . |
| 2054757 | 12/1990 | Canada . | | 42 17 761 | 2/1993 | Germany . |
| 1281734 | 3/1991 | Canada . | | 1-143846 | 6/1989 | Japan . |
| 2026467 | 3/1991 | Canada . | | 3-27308 | 6/1989 | Japan . |
| 1283121 | 4/1991 | Canada . | | 1-254727 | 10/1989 | Japan . |
| 1283663 | 4/1991 | Canada . | | 4-4219 | 1/1992 | Japan . |
| 2027887 | 4/1991 | Canada . | | 4-120540 | 4/1992 | Japan . |
| 2042587 | 4/1991 | Canada . | | 52106 | of 1937 | U.S.S.R. . |
| 2028728 | 5/1991 | Canada . | | 311 637 | 8/1971 | U.S.S.R. . |
| 2032556 | 6/1991 | Canada . | | 311 638 | 8/1971 | U.S.S.R. . |
| 2033405 | 7/1991 | Canada . | | 349 396 | 9/1972 | U.S.S.R. . |
| 2035650 | 8/1991 | Canada . | | 545 353 | 2/1977 | U.S.S.R. . |
| 2026417 | 9/1991 | Canada . | | 549 150 | 3/1977 | U.S.S.R. . |
| 2038332 | 9/1991 | Canada . | | 1 050 706 | 4/1982 | U.S.S.R. . |
| 1290766 | 10/1991 | Canada . | | 1 510 131 | 11/1986 | U.S.S.R. . |
| 2045762 | 12/1991 | Canada . | | 1 304 987 | 1/1973 | United Kingdom . |
| 2046373 | 1/1992 | Canada . | | 2 045 269 | 10/1980 | United Kingdom . |
| 1296015 | 2/1992 | Canada . | | 2 199 839 | 7/1988 | United Kingdom . |
| 2049725 | 3/1992 | Canada . | | 90/15083 | 12/1990 | WIPO . |
| 2061230 | 8/1992 | Canada . | | 90/15084 | 12/1990 | WIPO . |
| 2061539 | 8/1992 | Canada . | | 91/03502 | 3/1991 | WIPO . |
| 2041828 | 11/1992 | Canada . | | 93/10176 | 5/1993 | WIPO . |

LIQUID CRYSTALLINE (METH)ACRYLATE COMPOUNDS, COMPOSITION AND METHOD

This is a continuation-in-part of U.S. patent application Ser. No. 08/543,950 filed Oct. 17, 1995 (Case 1865), now abandoned. This is a continuation-in-part of U.S. patent application Ser. No. 08/217,998, filed Mar. 25, 1994, now U.S. Pat. No. 5,624,976 (Case 1718). This is a continuation-in-part of U.S. patent application Ser. No. 08/231,535 filed Apr. 22, 1994 (Case 1723), now abandoned.

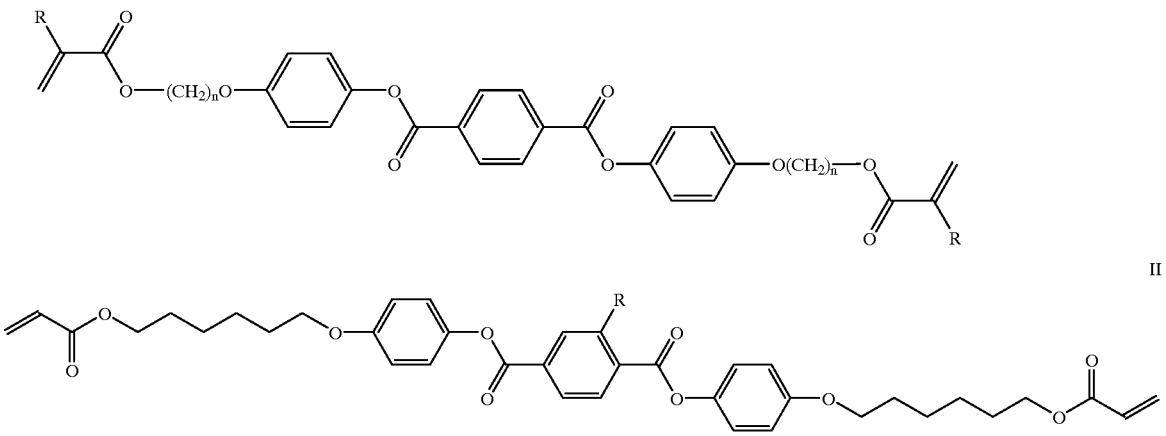

The invention relates to liquid crystalline (meth)acrylates suitable for dental and medical applications, as well as for optical, electrooptical application such as in liquid-crystal displays. The invention provides (meth)acrylate compounds which are liquid below 50° C., and are useful in compositions for treating natural teeth, such as dental restorative, cement, adhesive, primer, sealant and root canal filling compositions. The invention provides dental cement compositions and methods of using them for binding hard tooth material, metal and ceramic. The cement compositions include polymerizable ethylenically unsaturated monomers. The cements have superior adhesion to tooth without separately acid etching dentin or enamel. Compositions of the invention are useful as dental cements, liners, bases and restoratives. Compositions of the invention include less reactive diluent than prior art compositions. Compositions of the invention polymerize to form polymeric material having low or no residual monomer, preferably less than 1 percent residual monomer.

A series of acrylate, methacrylate or vinyl terminated compounds comprising a mesogenic or rigid rod-like moiety including (meth) acrylate terminated oligomers I and II with a mesogenic terephthaloyl ester moiety are disclosed by G. G. Barclay, C. K. Ober, Prog. Polym. Sci. 18 (1993) 899; D. J. Broer, G. N. Mol, Polym. Engng. Sci. 31 (1991) 625; R. A. M. Hikmet, J. Lub, J. A. Higgins, Polymer 34 (1993) 1736.

p-Hydroxy benzoic ester moieties incorporated into vinyl terminated compounds III are disclosed by D. J. Broer, J. Lub, G. N. Mol, Macromol. 26 (1993)1244.

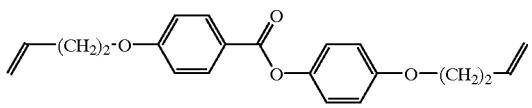

A diacrylate (wherein R is H) and a dimethacrylate (wherein R is $CH_3$) having the formula IV which comprises a biphenylhydroxy moiety is disclosed by H. Litt Morton, Wha-Tzong Whang, Kung-Ti Yen, Xue-Jun Qian, in J. Polym. Sci., Part $A_x$: Polym. Chem. 31 (1993) 183, Morton H. Lift US 89-369205.

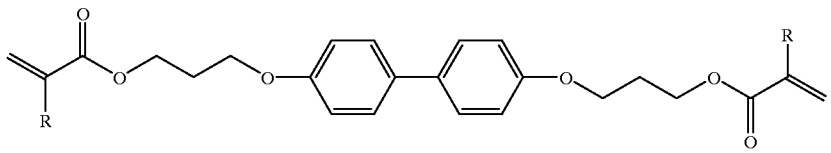

Acetylene terminated aromatic ester having the formula V are described by E. P. Douglas, Polymer Prep. 34 (1993) 702.

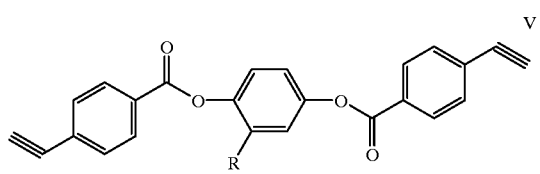

Methacrylates having the formula VI with a ridged rod-like moiety are disclosed in T. Shindo, T. Uryu, Liquid Crystals 15 (1993) 239).

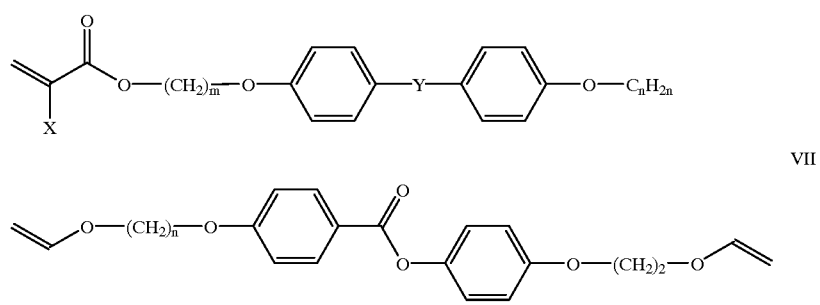

A vinyl terminated bishydroxybenzoate having formula VII which comprises spacers and exhibits relatively low phase transition temperatures only on cooling (n=11: i65n62s$_A$47s$_B$31k) and relatively narrow liquid crystalline phases, are disclosed by H. Anderson, F. Sahlen, and U. W. Gedde, A. Hult, in Macromol. Symp. (1994) 339.

Mixtures of (meth)acrylates comprising liquid crystalline monomers, dimethacrylates (2,2-Bis-[p-(2-hydroxy-3-methacryloyloxypropoxy)-phenyl]propane) and di(meth) acrylates comprising liquid crystalline monomers are described in EP 0379058.

However, the known liquid crystalline mono- or difunctional molecules have melting temperatures and liquid crystalline behavior at temperatures above 50° C. (Table 1 below, page 28). An application of these molecules in the liquid crystalline phase require temperatures over their melting temperature (50 to 170° C.). An application at room temperature is only possible in the solid state or in solution (25–30 volume % solvent).

In accordance with the invention monomers are provided which are liquid at room temperature and which show liquid crystalline behavior at least between 20 and 40° C. These liquid crystalline monomers are useful in dentistry, medicine, microelectronics and optoelectronics.

It is an object of the invention to provide a polymerizable compound within the scope of the general formula:

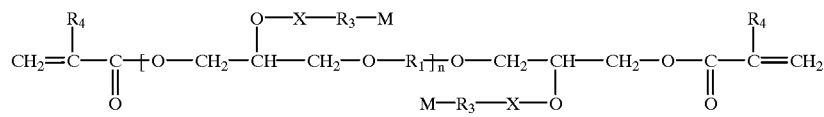

wherein
R$_1$ is a group of the general formula

-A-, -A-Y$_1$-B-, -A-Y$_1$-B-Y$_2$-C or a steroidal moiety, preferably selected of the group of cholesteryl compounds, wherein each A, B and C independently is a substituted or unsubstituted aromatic moiety having 6 to 24 carbon atoms, a substituted or unsubstituted heteroaromatic moiety having 2 to 24 carbon atoms or a substituted or unsubstituted cycloalkylene moiety having 5 to 30 carbon atoms, a substituted or unsubstituted alkylene moiety having 2 to 20 carbon atoms each Y$_1$ and Y$_2$ independently is a covalent bond, OCO, N=N, CH=N, C=C, CO, O(CO)O, O, S, SO$_2$, OCS, CH$_2$—O, CH$_2$—S,

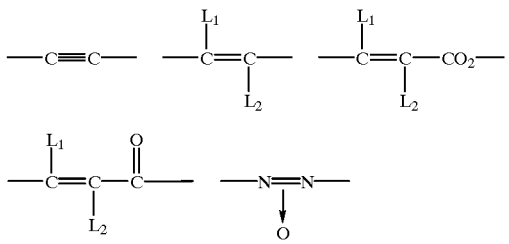

each L$_1$ and L$_2$ independently is a hydrogen, a alkylene having 1 to 20 carbon atoms or CN R$_3$ is a covalent bond or a substituted or unsubstituted alkylene having 1 to 20 carbon atoms, oxyalkylene having 1 to 20 carbon atoms, thioalkylene having 1 to 20 carbon atoms or a carboxyalkylene having 1 to 20 carbon atoms R$_4$ is hydrogen, a substituted or an unsubstituted alkyl having 1 to 20 carbon atoms, cycloalkyl having 5 to 12 carbon atoms, or aryl rest having 6 to 20 carbon atoms, M is a mesogenic group of the general formula

-A-Z, -A-Y$_1$-B-Z, -A-Y$_1$-B-Y$_2$-C-Z or a steroidal moiety, preferably selected of the group of cholesteryl compounds, wherein each A, B and C independently is a substituted or unsubstituted aromatic moiety having 6 to 24 carbon atoms, a substituted or unsubstituted heteroaromatic moiety having 2 to 24 carbon atoms or a substituted or unsubstituted cycloalkylene moiety having 5 to 30 carbon atoms each $Y_1$ and $Y_2$ independently is a covalent bond, OCO, N=N, CH=N, C=C, CO, O(CO)O, O, S, $SO_2$, OCS, $CH_2$—O, $CH_2$—S,

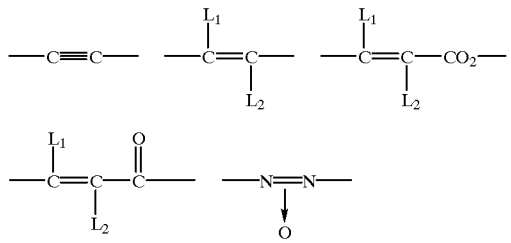

each $L_1$ and $L_2$ independently is a hydrogen, a alkylene having 1 to 20 carbon atoms or CN Z is a hydrogen, halogen, CN, —OR, COOR, $NO_2$, a halogen substituted or unsubstituted alkylene or alkenyl having 1 to 20 carbon atoms, a halogen substituted or unsubstituted oxyalkylene or oxyalkenyl having 1 to 20 carbon atoms, a halogen substituted or unsubstituted thioalkylene or thioalkenyl having 1 to 20 carbon atoms, a halogen substituted or unsubstituted carboxyalkylene or alkanoylenoxy having 1 to 20 carbon atoms, X is a covalent bond, CO, NHCO, OCO n is an integer from 1 to 10.

BRIEF DESCRIPTION OF THE INVENTION

Figure 1:
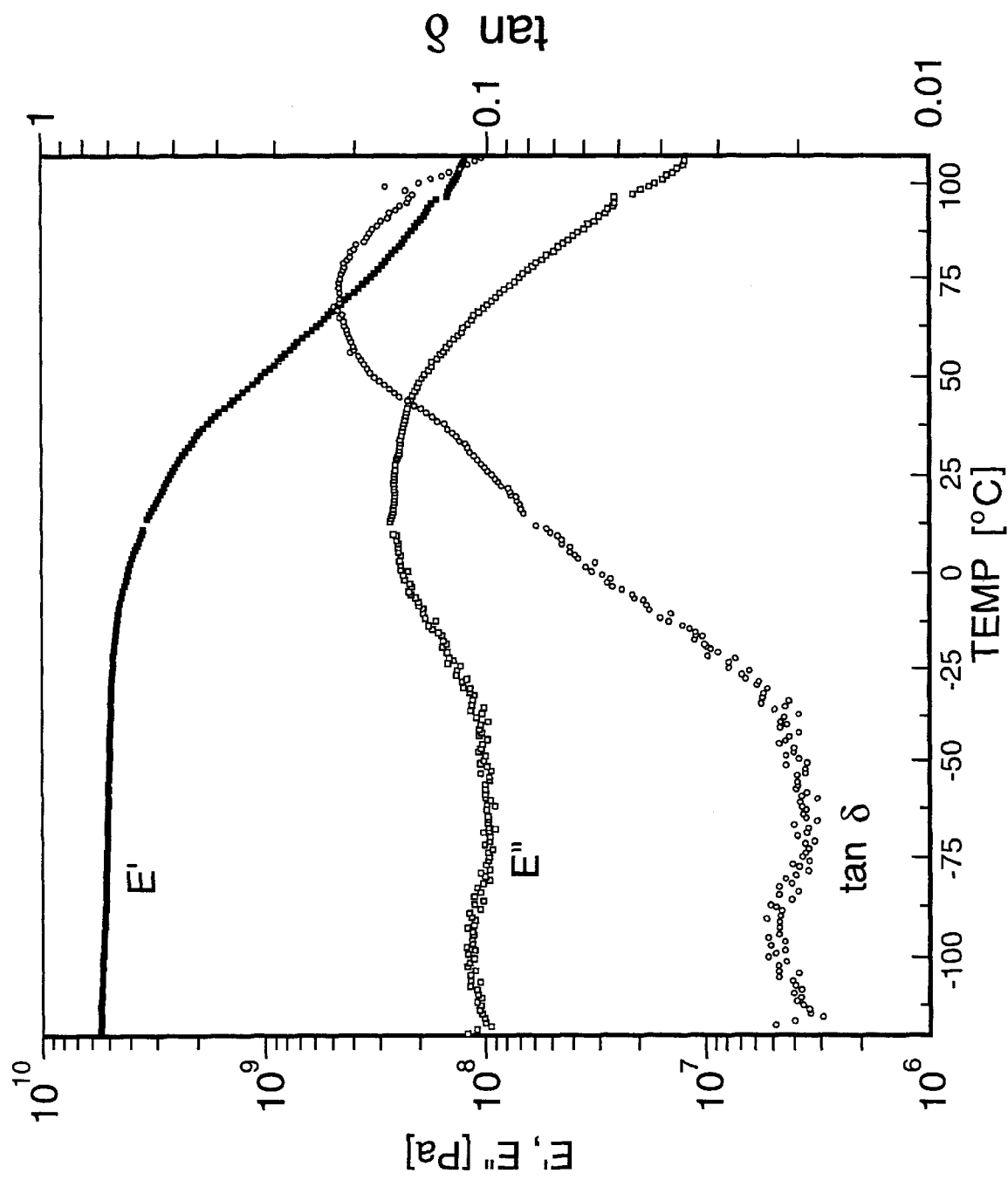
FIG. 1 is a graph of the thermomechanical properties of a composition in accordance with the invention.

The invention provides a polymerizable compound within the scope of the general formula:

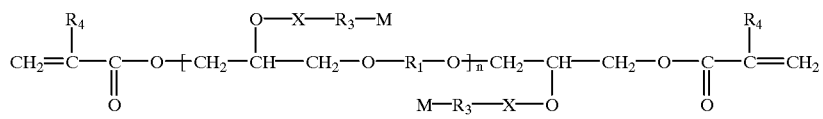

wherein $R_1$ is a group of the general formula -A-, -A-$Y_1$-B-, -A-$Y_1$-B-$Y_2$-C-, or a steroidal moiety, preferably selected of the group of cholesteryl compounds, wherein each A, B and C independently is a substituted or unsubstituted aromatic moiety having 6 to 24 carbon atoms, a substituted or unsubstituted heteroaromatic moiety having 2 to 24 carbon atoms or a substituted or unsubstituted cycloalkylene moiety having 5 to 30 carbon atoms, a substituted or unsubstituted alkylene moiety having 2 to 20 carbon atoms, each $Y_1$ and $Y_2$ independently is a covalent bond, OCO, N=N, CH=N, C=C, CO, O, S, $SO_2$, O(CO)O, OCS, $CH_2$—O, $CH_2$—S,

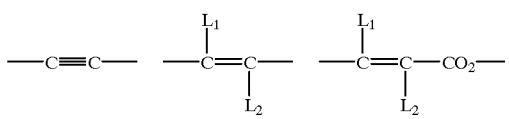

each $L_1$ and $L_2$ independently is a hydrogen, an alkyl having 1 to 20 carbon atoms, an alkylene having from 2 to 20 carbon atoms or CN, Alternatively, $R_1$ is expressed as a group of the general formula -$R_{10}$-, -$R_{10}$-$Z_1$-$R_{11}$-, -$R_{10}$-$Z_1$-$R_{11}$-$Z_2$-$R_{12}$-, or a steroidal moiety, preferably selected from the group of cholesteryl compounds, wherein each $R_{10}$, $R_{11}$, and $R_{12}$ independently is a substituted or unsubstituted aromatic moiety having 6 to 24 carbon atoms, a substituted or unsubstituted heteroaromatic moiety having 2 to 24 carbon atoms or a substituted or unsubstituted cycloalkylene moiety having 5 to 30 carbon atoms, a substituted or unsubstituted alkylene moiety having 2 to 20 carbon atoms, each $Y_1$ and $Y_2$ independently is a covalent bond, OCO, N=N, CH=N, C=C, CO, O, S, $SO_2$, O(CO)O, OCS, $CH_2$—O, $CH_2$—S,

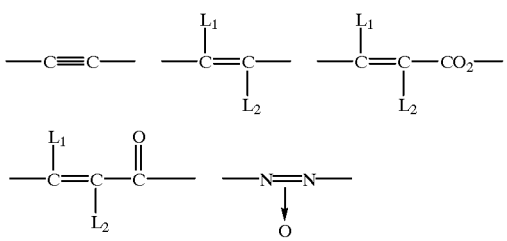

each $L_1$ and $L_2$ independently is a hydrogen, an alkyl having 1 to 20 carbon atoms, an alkylene having from 2 to 20 carbon atoms or CN, $R_3$ is a covalent bond or a substituted or unsubstituted alkylene having 1 to 20 carbon atoms, oxyalkylene having 1 to 20 carbon atoms, thioalkylene having 1 to 20 carbon atoms or a carboxyalkylene having 1 to 20 carbon atoms, $R_4$ is hydrogen, a substituted or an unsubstituted alkyl having 1 to 20 carbon atoms, cycloalkyl having 5 to 12 carbon atoms, or aryl rest having 6 to 20 carbon atoms, M is a mesogenic group of the general formula -A-Z, -A-$Y_1$-B-Z, -A-$Y_1$-B-$Y_2$-C-Z, or a steroidal moiety, preferably selected of the group of cholesteryl compounds, wherein each A, B and C independently is a substituted or unsubstituted aromatic moiety having 6 to 24 carbon atoms, a substituted or unsubstituted heteroaromatic moiety having 2 to 24 carbon atoms or a substituted or unsubstituted cycloalkylene moiety having 5 to 30 carbon atoms, each $Y_1$ and $Y_2$ independently is a covalent bond, OCO, N=N, CH=N, C=C, CO, O, S, $SO_2$, O(CO)O, OCS, $CH_2$—O, $CH_2$—S,

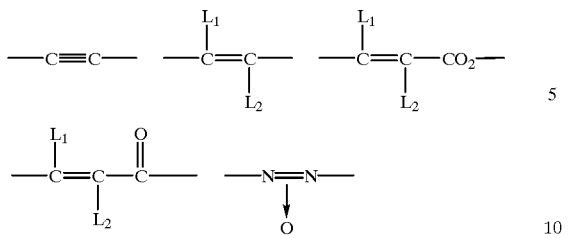

Alternatively, M is expressed as a mesogenic group of the general formula $-R_{10}-Z$, $-R_{10}-Z_1-R_{11}-Z$, $-R_{10}-Y_1-R_{11}-Z_2-R_{13}-$, or a steroidal moiety, preferably selected of the group of cholesteryl compounds, wherein each $R_{10}$, $R_{11}$ and $R_{12}$ independently is a substituted or unsubstituted aromatic moiety having 6 to 24 carbon atoms, a substituted or unsubstituted heteroaromatic moiety having 2 to 24 carbon atoms or a substituted or unsubstituted cycloalkylene moiety having 5 to 30 carbon atoms, each $Z_1$ and $Z_2$ independently is a covalent bond, OCO, N=N, CH=N, C=C, CO, O, S, $SO_2$, O(CO)O, OCS, $CH_2$—O, $CH_2$—S,

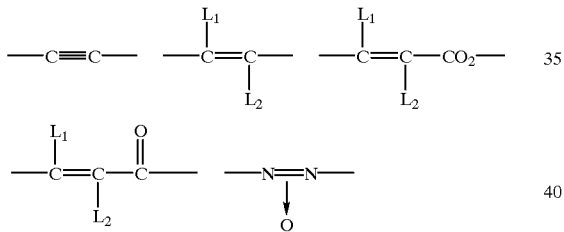

each $L_1$ and $L_2$ independently is a hydrogen, an alkyl having 1 to 20 carbon atoms, an alkylene having from 2 to 20 carbon atoms or CN, Z is a hydrogen, halogen, CN, —OR, COOR, $NO_2$, a halogen substituted or unsubstituted alkylene or alkylidene having 1 to 20 carbon atoms, a halogen substituted or unsubstituted oxyalkylene or oxyalkylidene having 1 to 20 carbon atoms, a halogen substituted or unsubstituted thioalkylene or thioalkylidene having 1 to 20 carbon atoms, a halogen substituted or unsubstituted carboxyalkylene or alkanoylenoxy having 1 to 20 carbon atoms, X is a covalent bond, CO, NHCO, OCO and n is an integer from 1 to 10.

DESCRIPTION OF THE INVENTION

Preparation of liquid crystalline (meth)acrylates

In accordance with the invention are prepared liquid crystalline (meth)acrylates within the scope of general formula 1 which have at least two polymerizable double bonds and at least two rigid rod-like moieties $R_1$ and M

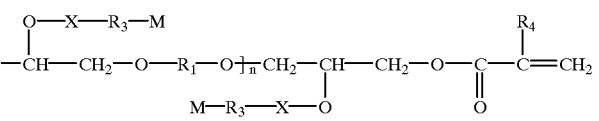

General formula 1 is alternatively written as general formula 1A as follows:

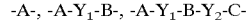

In formula 1 and 1A $R_1$ is a group of the general formula
$-A-$, $-A-Y_1-B-$, $-A-Y_1-B-Y_2-C-$
or a steroidal moiety, preferably selected of the group of cholesteryl compounds, wherein
each A, B and C independently is a substituted or unsubstituted aromatic moiety having 6 to 24 carbon atoms, a substituted or unsubstituted heteroaromatic moiety having 2 to 24 carbon atoms or a substituted or unsubstituted cycloalkylene moiety having 5 to 30 carbon atoms, a substituted or unsubstituted alkylene moiety having 2 to 20 carbon atoms each $Y_1$ and $Y_2$ independently is a covalent bond, OCO, N=N, CH=N, C=C, CO, O(CO)O, O, S, $SO_2$, OCS, $CH_2$—O, $CH_2$—S,

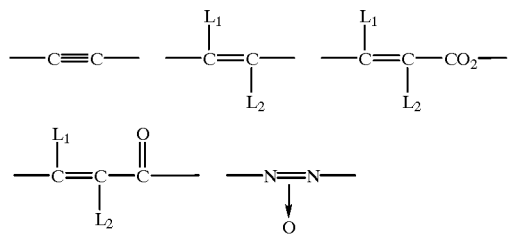

each $L_1$ and $L_2$ independently is a hydrogen, an alkyl having 1 to 20 carbon atoms, an alkylene having from 2 to 20 carbon atoms or CN $R_3$ is a covalent bond or a substituted or unsubstituted alkylene having 1 to 20 carbon atoms, oxyalkylene having 1 to 20 carbon atoms, thioalkylene having 1 to 20 carbon atoms or a carboxyalkylene having 1 to 20 carbon atoms $R_4$ is hydrogen, a substituted or an unsubstituted alkyl having 1 to 20 carbon atoms, cycloalkyl having 5 to 12 carbon atoms, or aryl rest having 6 to 20 carbon atoms, M is a mesogenic group of the general formula

-A-Z, -A-Y$_1$-B-Z, -A-Y$_1$-B-Y$_2$-C-Z or a steroidal moiety, preferably selected of the group of cholesteryl compounds, wherein

- each A, B and C independently is a substituted or unsubstituted aromatic moiety having 6 to 24 carbon atoms, a substituted or unsubstituted heteroaromatic moiety having 2 to 24 carbon atoms or a substituted or unsubstituted cycloalkylene moiety having 5 to 30 carbon atoms
- each Y$_1$ and Y$_2$ independently is a covalent bond, OCO, N=N, CH=N, C=C, CO, O(CO)O, O, S, SO$_2$, OCS, CH$_2$—O, CH$_2$—S,

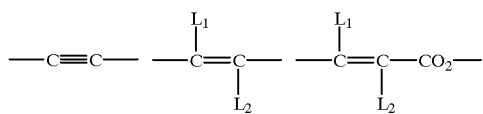

-continued

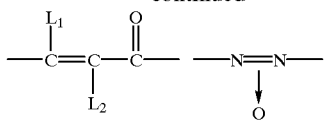

- each L$_1$ and L$_2$ independently is a hydrogen, an alkyl having 1 to 20 carbon atoms, an alkylene having from 2 to 20 carbon atoms or CN
- Z is a hydrogen, halogen, CN, —OR, COOR, NO$_2$, a halogen substituted or unsubstituted alkylene or alkenyl having 1 to 20 carbon atoms, a halogen substituted or unsubstituted oxyalkylene or oxyalkenyl having 1 to 20 carbon atoms, a halogen substituted or unsubstituted thioalkylene or thioalkenyl having 1 to 20 carbon atoms, a halogen substituted or unsubstituted carboxyalkylene or alkanoylenoxy having 1 to 20 carbon atoms,
- X is a covalent bond, CO, NHCO, OCO
- n is an integer from 1 to 10.

Compounds with the scope of general formulas A and B are within the scope of general formula 1 and 1A.

Preferably liquid crystalline (meth)acrylates have structures A and B.

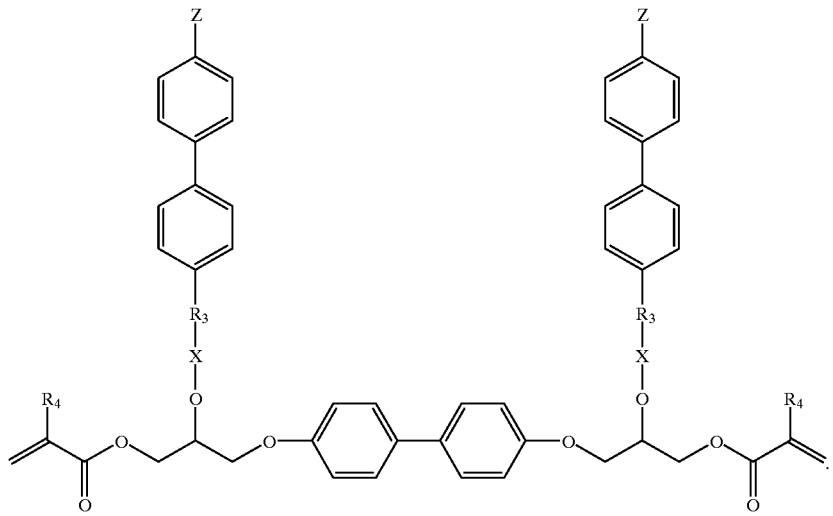

A

-continued

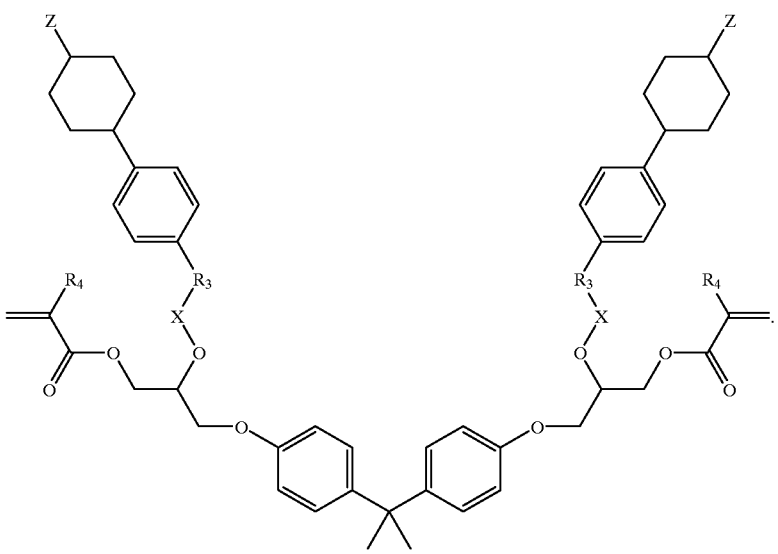
B

A macromonomer within the scope of general formula 5 is formed by reaction of a 2,3-epoxypropyl (meth)acrylate compound within the scope of general formula 4, a diphenol compound within the scope of general formula 3 and a diepoxide compound within the scope of general formula 2 as follows.

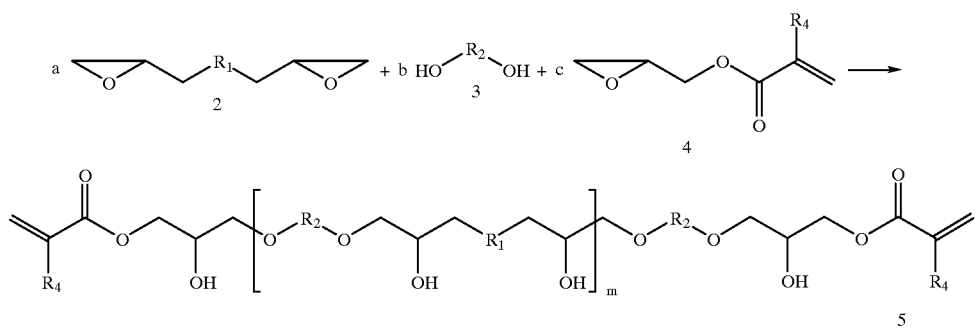

In general formulas 2 through 5 $R_2$ is a group of the general formula $$-A-, -A-Y_1-B-, -A-Y_1-B-Y_2-C-$$

or a steroidal moiety, preferably selected of the group of cholesteryl compounds, wherein

- each A, B and C independently is a substituted or unsubstituted aromatic moiety having 6 to 24 carbon atoms, a substituted or unsubstituted heteroaromatic moiety having 2 to 24 carbon atoms or a substituted or unsubstituted cycloalkylene moiety having 5 to 30 carbon atoms, a substituted or unsubstituted alkylene moiety having 2 to 20 carbon atoms
- each $Y_1$ and $Y_2$ independently is a covalent bond, OCO, N=N, CH=N, C=C, CO, O(CO)O, O, S, $SO_2$, OCS, $CH_2$—O, $CH_2$—S,

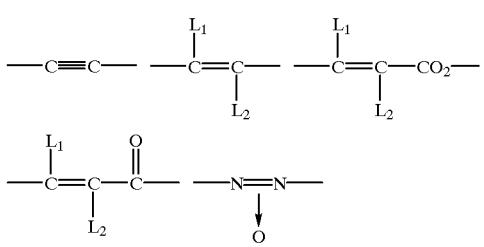

- each $L_1$ and $L_2$ independently is a hydrogen, an alkyl having 1 to 20 carbon atoms, an alkylene having from 2 to 20 carbon atoms or CN
- $R_4$ is hydrogen, a substituted or an unsubstituted alkyl having 1 to 20 carbon atoms, cycloalkyl having 5 to 12 carbon atoms, or aryl rest having 6 to 20 carbon atoms,
- $R_1$ is a substituted or unsubstituted aryl having from 6 to 24 carbon atoms and/or a substituted or unsubstituted cycloalkyl having from 5 to 12 carbon atoms. Preferably $R_1$ is

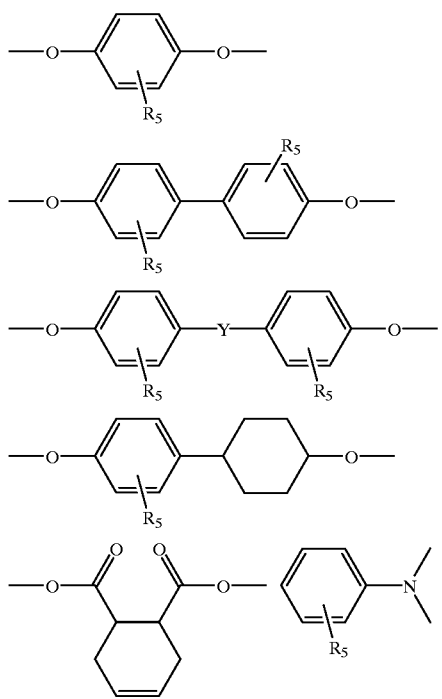

wherein $R_5$ is hydrogen, alkyl having from 1 to 12 carbon atoms, cycloalkyl having from 5 to 12 carbon atoms, aryl having from 6 to 18 carbon atoms and Y is substituted or unsubstituted alkylene having from 1 to 5 carbon atoms, 0, CO, OCO, S, $SO_2$ and, n is an integer from 1 to 10. Preferably n is 1, 2, or 3.

The reaction of epoxide di(meth)acrylates compounds within the scope of general formula 5 with organic acids within the scope of general formula 6 or derivatives thereof, with isocyanates within the scope of general formula 7 or alcohols 8 within the scope of general formula leads to modified di(meth)acrylates having ester moieties, urethane linkages or ether moieties 1 and 1A within the scope of general formula.

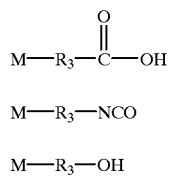

In the general formulas 6, 7 and 8 are $R_3$ is a covalent bond or a substituted or unsubstituted alkylene having 1 to 20 carbon atoms, oxyalkylene having 1 to 20 carbon atoms, thioalkylene having 1 to 20 carbon atoms or a carboxyalkylene having 1 to 20 carbon atoms M is a mesogenic group of the general formula $$-A-Z, -A-Y_1-B-Z, -A-Y_1-B-Y_2-C-Z$$

or a steroidal moiety, preferably selected of the group of cholesteryl compounds, wherein each A, B and C independently is a substituted or unsubstituted aromatic moiety having 6 to 24 carbon atoms, a substituted or unsubstituted heteroaromatic moiety having 2 to 24 carbon atoms or a substituted or unsubstituted cycloalkylene moiety having 5 to 30 carbon atoms each $Y_1$ and $Y_2$ independently is a covalent bond, OCO, N=N, CH=N, C=C, CO, O(CO)O, O, S, $SO_2$, OCS, $CH_2$—O, $CH_2$—S,

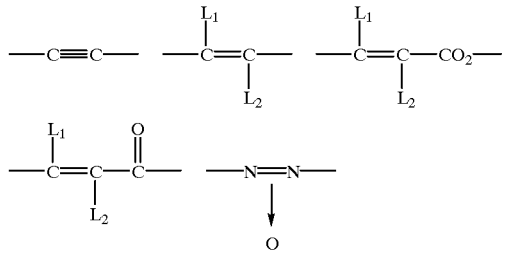

each $L_1$ and $L_2$ independently is a hydrogen, an alkyl having 1 to 20 carbon atoms, an alkylene having from 2 to 20 carbon atoms or CN Z is a hydrogen, halogen, CN, —OR, COOR, $NO_2$, a halogen substituted or unsubstituted alkylene or alkenyl having 1 to 20 carbon atoms, a halogen substituted or unsubstituted oxyalkylene or oxyalkenyl having 1 to 20 carbon atoms, a halogen substituted or unsubstituted thioalkylene or thioalkenyl having 1 to 20 carbon atoms, a halogen substituted or unsubstituted carboxyalkylene or alkanoylenoxy having 1 to 20 carbon atoms, The esterification, etherification and urethane formation of the di(meth)acrylate hydroxyl groups is carried out in solutions. As solvents for the esterification were used tetrahydrofurane, dioxane, $CH_2Cl_2$, DMF or others, or polymerizable monomers such as triethyleneglycol bismethacrylate, diethyleneglycol bismethacrylate, dioxolan bismethacrylate, vinyl-, vinylene- or vinylidene-, acrylate- or methacrylate substituted spiroorthoesters and 2,2-bis[p-(acryloxyethoxy)phenyl] propane.

For example a liquid crystalline di(meth)acrylate within the scope of structural formula 9 is synthesized in the following manner: 2,3-epoxy propoxy methacrylate and 4,4'-dihydroxy biphenyl are mixed and reacted for 15 hours at 115° C. to form a methacrylate terminated macromonomer having hydroxyl groups. The macromonomer hydroxyl groups are then esterified by mixing at 23° C. with 4'-cyano-biphenyl 4-oxy-valeric carboxylic acid and dicyclohexylcarbodiimid and than for further 24 hours at 23° C. to form a compound of the structural formula:

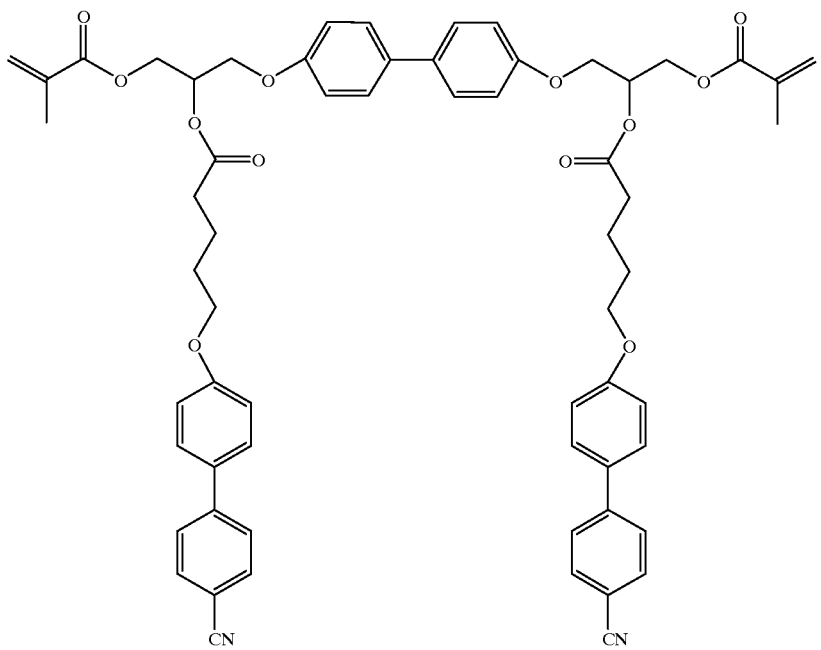

9

The compositions of the invention are formulated as one, two or more components, UV curable, visible light curable, self cure, and/or dual cure product or combinations of these. The composition of a preferred embodiment of the invention includes polymerizable carboxylic acid monomer, an optional filler and/or diluent, a cationic elutable glass or other source of polyvalent cations, and a polymerization catalyst system.

Fillers which are suited for use in compositions of the invention are organic and/or inorganic particles, for example inorganic glasses such as are used in glass ionomer cements. Exemplary of such fillers are those of U.S. Pat. No. 4,814,362 which is incorporated herein by reference in its entirety. Preferred fillers are glasses formed from or including, barium, calcium, strontium, lanthanum, tantalum, and/or tungsten silicates and aluminates and/or aluminosilicates, silica, including submicron silica, quartz, and/or ceramics for example, calcium hydroxy apatite. In a preferred embodiment of the invention reactive cations, especially those of calcium, strontium and aluminium, and anions especially fluoride ions; are eluted from the fillers. The fillers used in the invention preferably are reduced in particle size and are preferably silanated before they are incorporated into such compositions. Preferred levels of filler are from about 20% to about 85% based on the total weight of the composition, with from about 40% to about 85% being more preferable and about 50–80% being most preferred. If a more finely particulated filler is used, amounts of filler may be decreased due to the relative increase in surface area which attends the smaller sizes of particles. Preferred particle size distributions are from 0.02 to 50 microns, more preferably 0.1 to 10 microns, and most preferably 1 to 6 microns.

Mixing the compositions of the present invention may be achieved using standard compounding techniques. For example, liquids, photoinitiator(s), and accelerator(s) are blended first, and fillers are added incrementally thereafter. When blending light sensitive compositions, however, a photosafe room illumination, i.e., one that does not contain substantial amounts of wavelengths of electromagnetic radiation that would activate the photoinitiating system is used to avoid initiating polymerization of the composition prematurely.

The compounds of the present invention also have medical applications such as in self adhesive bone cements. However, they are most preferred to use in dental treatment by application to a tooth or a number of teeth in vivo, in the mouth of a live patient by a dentist or dental practitioner.

The application of the compositions of the invention is preferably as a polymerizable dental composition applied to tooth. In a preferred embodiment of the invention a dental cement composition includes a compound within the scope of general formula 1, and other ingredients, such as curing catalysts, initiators, accelerators, diluents and/or adjuvants. The composition is applied as a cement using conventional techniques and preferably cured with application of visible light in a conventional manner. Cements in accordance with the invention are self adhesive to dentin and enamel. These cements are used in bonding denin to structures, for example, to bond a ceramic inlay to a prepared cavity of a tooth. Inlays preferably are polymers, or ceramics which are cast or built-up from porcelain frits and fired. Alternatively, inlays are machined from metal such as titanium or gold or performed polymeric composite or homogeneous monolithic polymer compositions, for example by CAD-CAM procedures. In accordance with a preferred embodiment of the invention metal or ceramic superstructures for crowns, and bridges and/or orthodontic appliances are bonded to teeth using cement compositions of the invention. Such cement compositions join metal or ceramic to tooth by application of the cement composition by bringing them into contact until the cement hardens.

A preferred composition of the invention includes a two-part system. One part includes an initiator. The second part comprises filled and the co-initiator. The two parts are spatuled to form a cement prior to placement on tooth. The placement is by standard technique(s). Preferably the cement includes a visible light and/or a self-curing redox polymerization initiator system. In a preferred embodiment of the invention luting cement compositions have low viscosity and film thicknesses less than about 25 μm to bond close fitting appliances to prepared teeth. In one embodiment luting cement compositions of the present invention may be prepared of such high viscosity and consistency that they form adhesive "glue" lines of thicknesses up to several hundred microns to lute less close fitting restorations, for example inlays prepared using present state-of-the-art CAD-CAM devices. Compositions of the invention are mechanically strong, abrasion resistant, and are esthetically suitable and serve as the sole structural element to retain inlay, crowns and bridges or other appliances to tooth structure.

A preferred dental treatment in accordance with the invention is the application of dental filling compositions which include an initiator and at least one compound within the scope of general formula 1. Preferably the dental filling composition includes finely divided filler. Preferably the composition is applied to a tooth as a filling material using conventional techniques as a one-component material and is cured with application of visible light in conventional manner.

In a preferred embodiment of the invention a one or two component pit and fissure sealant which includes at least one compound within the scope of general formula 1 is applied to anatomic defects and/or the exterior of teeth. The sealant limits the ability of caries-forming bacteria to colonize the pits, fissures and other surfaces of the teeth. Pit and fissure sealant compositions in accordance with the invention are an especially valuable means of reducing caries by filling and eliminating enamel defects. The pit and fissure sealants of the invention are preferably applied with or without prior acid etching or the use of rubber dam to teeth. In one embodiment fluoride eluting compounds and glasses are preferably included in compositions of the invention. Fluoride is eluted to reduce the incidence of caries in tooth substance adjacent the compositions of the invention.

Preferred compositions of the invention include two or more ethylenically unsaturated materials are included in compositions of the invention. The polymerizable monomer is preferably liquid at 23° C., and comprises from about 0.5 to about 99.998% by weight of the composition, with amounts ranging from about 1 to about 99.98% being preferred, and amounts ranging from about 1.5 to about 99.8% being more preferred.

Preferred compositions of the invention include an adhesion promoter for example a phosphorus-containing adhesion promoter which is free from any halogen atoms covalently or otherwise bonded directly to a phosphorus atom. The phosphorus derivative may be polymerizable or non-polymerizable, however the preferred phosphorus-containing adhesion promoters comprise polymerizable phosphorus materials having ethylenic unsaturation and include, among others, organic esters of one or more acids of phosphorus (hereinafter referred to as phosphorus acid esters), wherein the organic portion of the ester contains at least one polymerizable ethylenically unsaturated group. The organic portion of the ester may be alkenyl, alkenoxy, cycloalkenyl, aralkenyl, or alkenaryl, and preferably may have from 2 to 40 carbon atoms. The organic portion may be straight chain, branched, or cyclic, can contain skeletal hetero atoms, i.e., atoms other than carbon, and can be unsubstituted or substituted with moieties which do not interfere with the free radical polymerization of the phosphorus acid esters.

Examples of saturated and unsaturated phosphorus acid esters which may be used include, but are not limited to, monomers containing phosphoric acid groups such as hydroxyethyl methacrylate monophosphate, 2,2,'-bis(alpha -methacryloxy- beta -hydroxypropoxyphenyl) propane diphosphonate (BIS-GMA diphosphonate), BIS-GMA diphosphate, dibutyl phosphite, di-2-ethylhexyl phosphite, di-2-ethylhexyl phosphate, glyceryl-2-phosphate, glycerylphosphoric acid, methacryloxyethyl phosphate, and glyceryl dimethacrylate phosphate. Other suitable polymerizable phosphorus acid esters are disclosed, for example, in U.S. Pat. No. 4,499,251 to Omura et al, U.S. Pat. No. 4,222,780 to Shibantani et al, U.S. Pat. No. 4,235,633 to Tomioka, U.S. Pat. No. 4,259,117 to Yamauchi et al, U.S. Pat. No. 4,368, 043 to Yamauchi et al. Of the polymerizable phosphorus acid compounds disclosed in the above patents and application, each of which is incorporated herein by reference, the preferred compounds are those polyethylenically unsaturated monophosphates of the formula:

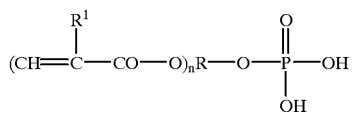

and salts thereof, in which

R is an organic radical having a valency of n+1; and R may be interrupted by one or more oxygen atoms and may be substituted or unsubstituted, and may comprise an aliphatic radical, or a cycloaliphatic radical, or an aryl radical;

$R^1$ is a hydrogen atom, alkyl having from 1 to 3 carbon atoms, halogen or —C≡N, and n is an integer of at least 1. Preferably n is an integer of 2 or more, and more preferably from 3 to 6. Examples of the preferred compounds include pentaerythritol triacrylate monophosphate, pentaerythritol trimethacrylate monophosphate, dipentaerythritol pentaacrylate monophosphate, and dipentaerythritol pentamethacrylate monophosphate. When included the phosphorus acid compound may comprise from about 0.25 to about 99.998% by weight of the adhesive composition, with amounts ranging from about 1 to about 50% being preferred. In a more preferred embodiment the phosphorus acid compound would comprise from about 2 to about 29.8% by weight of the composition.

Preferred compositions of the invention include a catalyst component which may comprise any free radical initiators normally used in conjunction with polymerizable ethylenically unsaturated materials, although those which will initiate polymerization at room temperature are more preferred. Thus, the catalyst may comprise, for example, an organic peroxide type initiator such as dibenzoyl peroxide, dilauroyl peroxide, acetyl peroxide, t-butyl peroxybenzoate, cumene hydroperoxide and the like. In a preferred aspect, the catalyst comprises an actinic light sensitive initiator, such as ultraviolet light-sensitive initiators or visible light sensitive initiators. As examples of suitable ultraviolet light-sensitive initiators there may be mentioned the monoketals of an aromatic 1,2-diketone, benzophenones, substituted benzophenones, benzoin methyl ether, isopropoxybenzoin, benzoin phenyl ether or benzoin isobutyl ether. Among the suitable visible light sensitive initiators, alpha-diketones, such as camphoroquinone, are particularly preferred. The preferred initiators are the visible light sensitive initiators. The catalyst generally is employed in the range of from about 0.001 to about 10% of the composition. In a preferred embodiment the catalyst is used within the range of from 0.01 to about 5%. In a still further preferred embodiment, from about 0.1 to about 2% by weight of catalyst is employed.

In a preferred embodiment of the invention, polymerizable compositions are provided which include an accelerator system comprising (1) an amine or amine salt and/or (2) a sulfinic acid or salt thereof and/or (3) a metal salt or organo metal compound. In a preferred embodiment both the amine or amine salt and the sulfinic acid or salt thereof are present. The amine or amine salt may be present in an amount from 0 to about 20% by weight of the composition, whereas the sulfinic acid or salt thereof is present in an amount of from about 0 to about 10%, the combined amount being from about 0.001 to about 20 percent. In a preferred embodiment, the amine or amine salt is in the range of 0.001 to about 10% by weight of the polymerizable composition, and the sulfinic acid or a sulfinic acid salt is in the range from about 0.01 to about 5 percent by weight of the polymerizable composition, the combined weight being in the range from about 0.01–15% by weight. In a still more preferred embodiment, the amine or amine salt is in an amount from about 0.1–8 percent by weight of the polymerizable composition and the sulfinic acid or salt thereof is in an amount from 0.1–2 percent by weight of the polymerizable composition, the combined amount ranging from about 0.2 to 10 percent by weight of the polymerizable composition.

The amine or amine salt employed in a preferred embodiment of this invention desirably is a secondary or tertiary amine rather than a primary amine, since the use of a secondary or tertiary amine leads to significantly accelerated curing. Examples of suitable amines include N,N-dimethylaniline, N,N-dimethyl-p-toluidine, N-methyl-N-beta-hydroxyethylaniline.

Primers and adhesives of the invention may be filled to such an extent that they would serve not only as primers and adhesives, but also as pit and fissure sealants and dental filling composites. A primer, composition of the invention comprises by weight about 5–20% PENTA, 0–61% hydroxyethyl methacrylate, 0.1% butylated hydroxytoluene.

All of the percentages recited herein are by weight based on the weight of the entire composition unless otherwise stated.

EXAMPLE 1
Synthesis of 4.4'-Bis-(2-hydroxy-3-methacryloylpropoxy)-biphenyl 60.00 g (0.422 mol) 2,3-Epoxypropoxy methacrylate, 0.40 g 2,6-Di-tert.-butyl-cresol, 39.3 g (0.211 mol) 4,4'-Dihydroxybiphenyl and 250 ml 1-Methoxy-2-propanol are heated until a homogeneous clear liquid is formed. After adding 0.30 g 1,8-Diaza-bicyclo-[5.4.0]-undec-7-ene the mixture were kept for 15 hours at 115° C. Then the mixture is concentrated and dropped into petrolether and cooled onto 0° C. The separated solid is filtered and washed with petrolether and dried. The crude product is recrystallized from 200 ml ethanol dissolved in a small amount DMSO and filtered over $Al_2O_3$ (act. II/III, app. 500 g) using acidic ethyl ester/petrol ether. After removing the solvents 14 g of pure 4,4'-Bis-(2-hydroxy-3-methacryloylpropoxy)-biphenyl is obtained.

$^1$H NMR: 7.6/7.05 (Ar), 6.1/5.7 ($CH_2$=C—), 5.45 (OH), 4.3, 4.1 (CH, $CH_2$OCO), 4.0 ($CH_2$OAr), 1.9 ($CH_3$).

$^{13}$C NMR: 166.3 (CO), 157.4/132.3/127.1/114.7 (Ar), 135.6 (C=), 125.8 ($CH_2$=), 69.0 ($CH_2$O), 66.6 (CH), 65.5 ($CH_2$OCO), 17.8 ($CH_3$).

Esterification of 4.4'-bis-(2-hydroxy-3-methacryloylpropoxy)-biphenyl with 4'-Cyano-biphenyl-4-oxyvaleric carboxylic acid 6,50 g (22 mmol) 4'-Cyano-biphenyl-4-oxyvalerian carboxylic acid, 4,71 g (10 mmol) 4,4'-bis-(2-hydroxy-3-methacryloylpropoxy)-biphenyl and 0,25 g dimethylamino pyridine were dissolved in 85 ml $CH_2Cl_2$/DMF (vol.-ratio 9:8). To the mixture were added 5,00 g (24,2 mmol) dicyclohexyl carbodiimid. Then the mixture were stirred for 24 hours at room temperature. After this time the precipitated solid was filtered off. To the filtrate were added 0,1 g BHT and the solvent was removed by vacuum distillation. The viscose residue was dissolved in 100 ml $CH_2Cl_2$ and cooled to 0° C. The precipitating solid was removed and the filtrate was washed twice with 50 ml 1 n HCl, 50 ml 1 n $NaHCO_3$ solution and with 150 ml water and filtered over silica. Furthermore, the solution was dried over $NaSO_4$ and the solvent was removed to obtain 5.5 g of 4,4'-bis-(2-hydroxy-3-methacryloylpropoxy)-biphenyl esterified with 4'-Cyano-biphenyl-4-oxyvaleric carboxylic acid.

APPLICATION EXAMPLE 1

To 5.00 g liquid crystalline di(meth)acrylate of Example 1 are added and 0,05 g JRAGCURE 651 (Ciba—Geigy). Using a curing unit (Dentsply De Trey) the mixture is polymerized by irradiation with visible light during 40 seconds. The degree of polymerization is about 85%. The obtained material shows a volume shrinkage of 2.4 percent. The thermo-mechanical properties are shown in FIG. 1 wherein E' (storage modulus) is $2.8 \cdot 10^9$ Ps (25° C.), E" (loss modulus) is $2.9 \cdot 10^8$ Pa (25° C.) and tan δ (E"/E') is 0.22.

COMPARATIVE EXAMPLE 1

To 7.000 g of (2,2-Bis-[p-(2-hydroxy-3-methacryloyloxypropoxy)-phenyl]propane) and 3.000 g of triethyleneglycol dimethacrylate were added 0,050 g N,N-di-(β-hydroxyethyl)-p-toluidine and 0.050 g champhorquinone. Using a curing unit (Dentsply De Trey) the mixture was polymerized by irradiation with visible light during 40 seconds. The degree of polymerization is about 65%. The obtained material shows a volume shrinkage of 6.5 percent.

Synthesis of 4,4'-bis-(2-hydroxy-3-methacryloylpropoxy)-biphenyl as described in example 1

Esterification of 4,4'-bis-(2-hydroxy-3-methacryloylpropoxy)-biphenyl with 4'-Cyano- biphenyl-4-oxyundecane carboxylic acid 11.39 g (30 mmol) 4'-Cyano-biphenyl-4-oxyundecane carboxylic acid, 6.59 g (14 mmol) 4,4'-bis-(2-hydroxy-3-methacryloylpropoxy)-biphenyl and 0.32 g (2,6 mol) dimethylamino pyridine were dissolved in 160 ml $CH_2Cl_2$/DMF (having a volume ratio 5:3). To the mixture were added 6,60 g (32 mmol) dicyclohexyl carbodiimid. Then the mixture were stirred for 27 hours at room temperature. After this time the precipitated solid was filtered off. To the filtrate were added 0.15 g BHT and the solvent was removed by vacuum distillation. The viscose residue was dissolved in 250 ml $CH_2Cl_2$ and cooled to 0° C. The precipitating solid was removed and the filtrate was washed twice with 150 ml with 1 n HCl, 150 ml 1 n $NaHCO_3$ solution and with 75 ml water and filtered over silica. Furthermore, the solution is dried over $NaSO_4$ and the solvent is removed.

Yield: 6.9 g

Table 1 shows the Melting Points (° C.) of LC-Monomers II–VI and the glass transition temperatures of Examples 1 and 2.

| LC-Monomer | R/X | Melting point (° C.) |
| --- | --- | --- |
| II | H | 108 |
| II | CH₃ | 86 |
| III | — | 52 |
| IV |  | 84 |
| V | Cl | 157 |
| V | OCH₃ | 154 |
| V | CH₃ | 169 |
| VI | H | 87–89 |
| VI | CH₃ | 98–99 |
| Example 1 |  | 18* |
| Example 2 |  | 6** |

*At 18° C. the glassy product of Example 1 becomes a liquid and from 18 to 67.5° C. remains in the nematic phase.
**At 6° C. the glassy product of Example 2 becomes a liquid and from 6 to 59.5° C. remains in the nematic phase.

EXAMPLE 3

Self-Curing, Two Component, Powder and Liquid Cement 0.92 grams of the dried product prepared as described in Example 2 and 0.08 grams of triethyleneglycol dimethacrylate are dissolved in one another to form a liquid. 1.0 grams of this liquid is added to 2.0 grams of the strontium aluminofluorosilicate containing powder. The consistency of the mixture is suitable for use as a luting or crown and bridge or orthodontic cement or as a filling material. Polymerization is induced by the redox polymerization system of benzoyl peroxide, ascorbyl palmitate and copper acetyl acetonate. The powder and liquid compositions are as follows:

|  | PERCENT BY WEIGHT |
| --- | --- |
| POWDER |  |
| Strontium fluoroaluminosilicate cement (Glass) | 98.83 |
| Benzoyl peroxide | 1.00 |
| ascorbyl palmitate | 0.15 |
| copper acetyl acetonate | 0.02 |
| LIQUID |  |
| Product of example 2 | 92.00 |
| Triethylene glycol dimethacrylate | 8.00 |

The powder and liquid are mixed in a 1:1 ratio by volume to form a cement. This cement is adhesive to dentin and enamel without further treatment except cleansing with pumice.

EXAMPLE 4

Esterification of (2,2-Bis-[p-(2-hydroxy-3-methacryloyloxypropoxy)-phenyl]propane) with 11-[4'(trans-4-propyl-cyclohexyl)-phenoxy]-undecane carboxylic acid 1.50 g (3.73 mmol) 11-[4'(trans-4-propyl-cyclohexyl)-phenoxy]-undecane carboxylic acid. 0.87 g (1.69 mmol) (2.2-Bis-[p-(2-hydroxy-3-methacryloyloxypropoxy)-phenyl]-propane) and 0.05 g dimethylamino pyridine were dissolved in 20 ml $CH_2Cl_2$. To the mixture were added 0.85 g (4.10 mmol) dicyclohexyl carbodiimid at 0° C. Then the mixture stirred for 24 hours at room temperature. After this time the precipitated solid was filtered off. To the filtrate were added 0.05 g BHT and the solvent was removed by vacuum distillation. The viscose residue was washed with pentane and filtered over aluminum oxide. The separation of the disubstituted product from mono-substituted impurities occurs by column chromatography(silica, $CHCl_3$). After evaporation of the solvent was obtained a highly viscous, slightly yellow liquid crystalline substance. The liquid crystalline dimethacrylate exhibits a glass transition temperature of $T_g$ –10° C. It shows a liquid crystalline behavior between –10 and 19° C. (smectic phase). The yield is 0.77 g.

$^{13}$C-NMR: 14.4 ($CH_2$—$\underline{C}H_3$). 18.3 (C=C—$\underline{C}H_3$). 20.1 ($\underline{C}H_2$—$CH_3$). 24.9–37.0 (aliphatic $CH_2$ and cyclohexyl). 29.5 (C—$\underline{C}H_3$). 39.8 ($CH_2$-cyclohexyl). 43.7 ($\underline{C}$—$CH_3$). 62.9 (COO—$CH_2$). 66.3 (Ph—O$\underline{C}H_2$). 69.4 (CH—O). 114.2–135.8 (aromatic carbons). 126.2 (=$CH_2$). 135.8 (=C). 157.2–157.5 (aromatic carbons). 166.9 (=C($\underline{C}O_2$)—). 173.1 (($CH_2$)$_4$—$\underline{C}O_2$—).

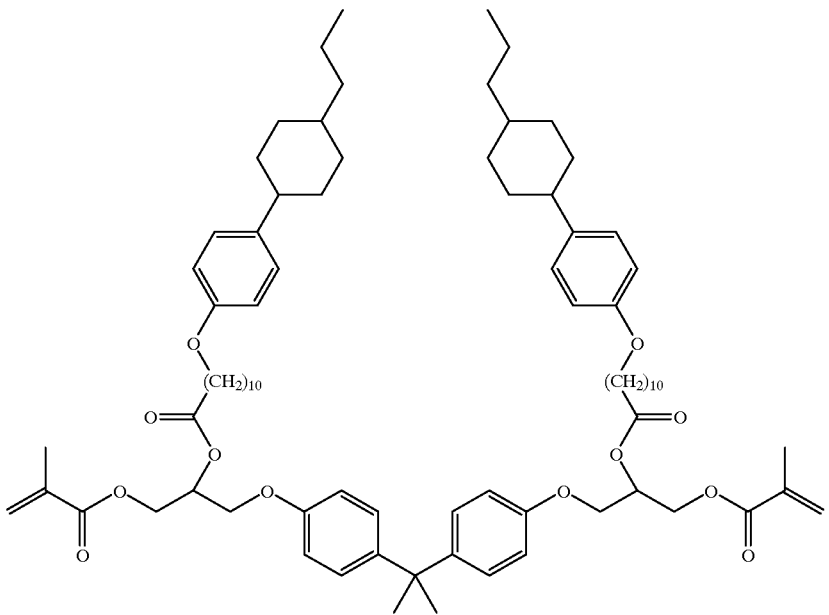

It should be understood that while the present invention has been described in considerable detail with respect to certain specific embodiments thereof, it should not be considered limited to such embodiments but may be used in other ways without departure from the spirit of the invention and the scope of the appended claims.

What we claim is:

1. A polymeric product formed by polymerization of a liquid crystalline compound within the scope of the general formula:

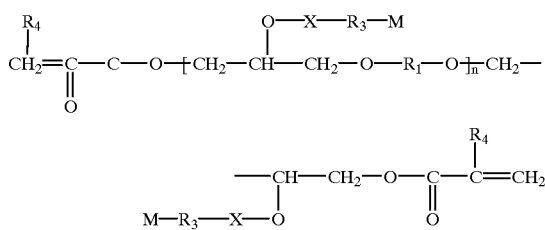

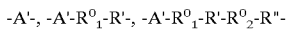

wherein $R_1$ is a group of the general formula

-A'-, -A'-$R^0_1$-R'-, -A'-$R^0_1$-R'-$R^0_2$-R"- or a steroidal moiety, wherein each A', R' and R" independently is a substituted or unsubstituted aromatic moiety having 6 to 24 carbon atoms, a substituted or unsubstituted heteroaromatic moiety having 6 to 24 carbon atoms or a substituted or unsubstituted cycloalkylene moiety having 5 to 30 carbon atoms, a substituted or unsubstituted alkylene moiety having 2 to 20 carbon atoms each $R^0_1$ and $R^0_2$ independently is a covalent bond, OCO, N=N, CH=N, C=C, CO, O(CO)O, O, S, $SO_2$, OCS, $CH_2$—O, $CH_2$—S,

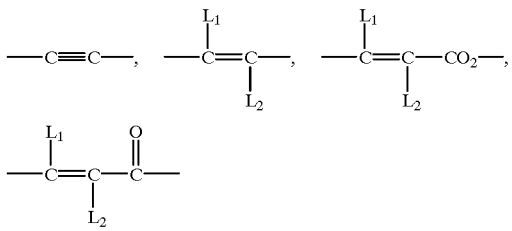

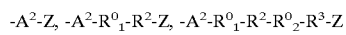

each $L_1$ and $L_2$ independently is hydrogen, alkyl having 1 to 20 carbon atoms, alkylene having 2 to 20 carbon atoms or CN $R_3$ is a covalent bond, alkylene having 1 to 20 carbon atoms, halogen substituted or unsubstituted alkylene having 2 to 20 carbon atoms, oxyalkylene having 1 to 20 carbon atoms, thioalkylene having 1 to 20 carbon atoms or a carboxyalkylene having 1 to 20 carbon atoms $R^4$ is hydrogen, a substituted or an unsubstituted alkyl having 1 to 20 carbon atoms, cycloalkyl having 5 to 12 carbon atoms, or aryl having 6 to 20 carbon atoms, M is a mesogenic group comprising two rings and of the general formula

-$A^2$-Z, -$A^2$-$R^0_1$-$R^2$-Z, -$A^2$-$R^0_1$-$R^2$-$R^0_2$-$R^3$-Z or a steroidal moiety, wherein each $A^2$ independently is a substituted or unsubstituted aromatic moiety having up to 24 carbon atoms, a substituted or unsubstituted heteroaromatic moiety having up to 24 carbon atoms each $R^2$ and $R^3$ independently is a substituted or unsubstituted aromatic moiety having up to 24 carbon atoms, a substituted or unsubstituted heteroaromatic moiety having up to 24 carbon atoms or a substituted or unsubstituted cycloalkylene moiety having up to 30 carbon atoms each $R^0_1$ and $R^0_2$ independently is a covalent bond, OCO, N=N, CH=N, C=C, CO, O(CO)O, O, S, $SO_2$, OCS, $CH_2$—O, $CH_2$—S,

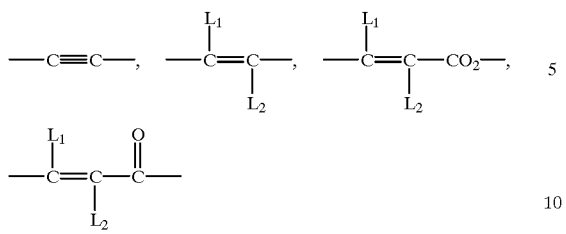

each $L_1$ and $L_2$ independently is hydrogen, alkyl having 1 to 20 carbon atoms, alkylene having 2 to 20 carbon atoms or CN Z is a hydrogen, CN, —OR, COOR, $NO_2$, alkyl having 1 to 20 carbon atoms, halogen substituted or unsubstituted alkylene or alkenyl having 2 to 20 carbon atoms, a halogen substituted or unsubstituted oxyalkylene or oxyalkenyl having up to 20 carbon atoms, a halogen substituted or unsubstituted thioalkylene or thioalkenyl having up to 20 carbon atoms, a halogen substituted or unsubstituted carboxyalkylene or alkanoylenoxy having up to 20 carbon atoms, X is a covalent bond, CO, NHCO, OCO n is an integer from 1 to 10, said liquid crystalline compound being in a mesomorphic state, said product comprising less than one percent by weight of said compound.

2. A liquid crystalline compound within the scope of the general formula:

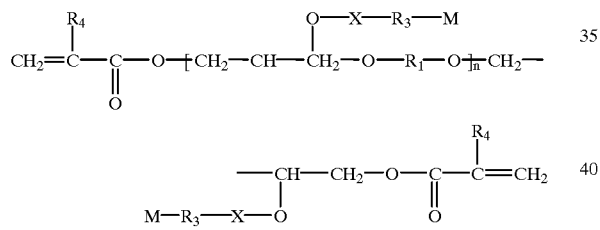

wherein $R_1$ is a group of the general formula

-A'-, -A'-$R^0_1$-R'-, -A'-$R^0_1$-R'-$R^0_2$-R"- or a steroidal moiety, wherein each A', R' and R" independently is a substituted or unsubstituted aromatic moiety having 6 to 24 carbon atoms, a substituted or unsubstituted heteroaromatic moiety having 6 to 24 carbon atoms or a substituted or unsubstituted cycloalkylene moiety having 5 to 30 carbon atoms, a substituted or unsubstituted alkylene moiety having up to 20 carbon atoms each $R^0_1$ and $R^0_2$ independently is a covalent bond, OCO, N=N, CH=N, C=C, CO, O(CO)O, O, S, $SO_2$, OCS, $CH_2$—O, $CH_2$—S,

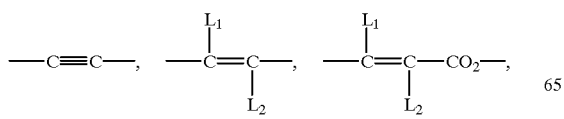

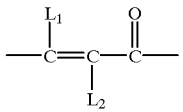

each $L_1$ and $L_2$ independently is a hydrogen, alkyl having 1 to 20 carbon atoms, alkylene having 2 to 20 carbon atoms or CN $R_3$ is a covalent bond or halogen substituted or unsubstituted alkylene having 1 to 20 carbon atoms, oxyalkylene having 1 to 20 carbon atoms, thioalkylene having 1 to 20 carbon atoms or a carboxyalkylene having 1 to 20 carbon atoms $R_4$ is hydrogen, a substituted or an unsubstituted alkyl having 1 to 20 carbon atoms, cycloalkyl having 5 to 12 carbon atoms, or aryl having 6 to 20 carbon atoms, M is a mesogenic group comprising two rings and of the general formula

-$A^2$-Z, -$A^2$-$R^0_1$-$R^2$-Z, -$A^2$-$R^0_1$-$R^2$-$R^0_2$-$R^3$-Z or a steroidal moiety, wherein each $A^2$ independently is a substituted or unsubstituted cycloalkylene moiety having up to 30 carbon atoms each $R^2$ independently is a substituted or unsubstituted aromatic moiety having up to 24 carbon atoms, a substituted or unsubstituted heteroaromatic moiety having up to 24 carbon atoms each $R^3$ independently is a substituted or unsubstituted aromatic moiety having up to 24 carbon atoms, a substituted or unsubstituted heteroaromatic moiety having up to 24 carbon atoms or a substituted or unsubstituted cycloalkylene moiety having up to 30 carbon atoms, a substituted or unsubstituted alkylene moiety having up to 20 carbon atoms each $R^0_1$ and $R^0_2$ independently is a covalent bond, OCO, N=N, CH=N, C=C, CO, O(CO)O, O, S, $SO_2$, OCS, $CH_2$—O, $CH_2$—S,

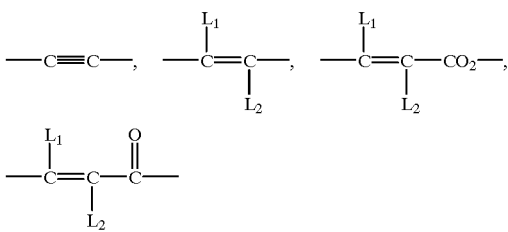

each $L_1$ and $L_2$ independently is a hydrogen, alkyl having 1 to 20 carbon atoms, alkylene having 2 to 20 carbon atoms or CN Z is a hydrogen, halogen, CN, —OR, COOR, $NO_2$, a halogen substituted or unsubstituted alkylene or alkenyl having 1 to 20 carbon atoms, a halogen substituted or unsubstituted oxyalkylene or oxyalkenyl having up to 20 carbon atoms, a halogen substituted or unsubstituted thioalkylene or thioalkenyl having up to 20 carbon atoms, a halogen substituted or unsubstituted carboxyalkylene or alkanoylenoxy having up to 20 carbon atoms, X is a covalent bond, CO, NHCO, OCO n is an integer from 1 to 10, said liquid crystalline compound being in a mesomorphic state.

3. The compound of claim 1 wherein the liquid crystalline (meth)acrylate is within the scope of formula:

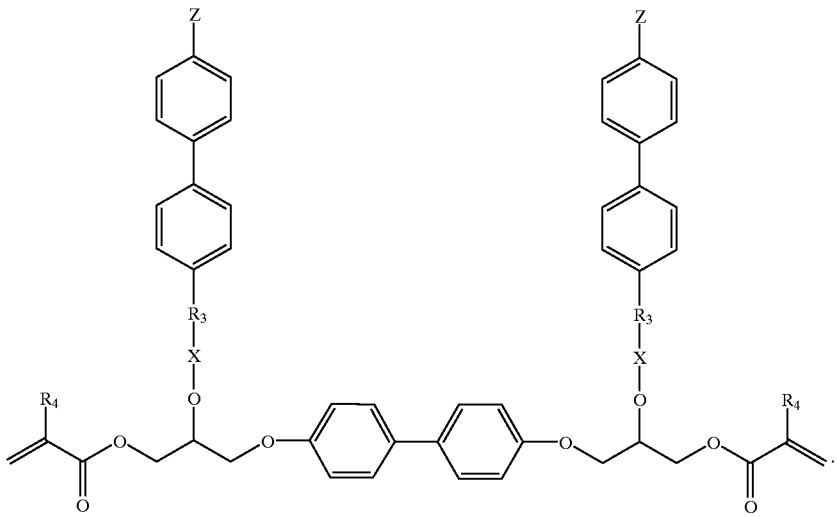

4. The compound of claim 2 wherein said compound is made by etherification, esterification or formation of urethane linkages of at least a portion of the —OH groups of a macromonomer having at least two terminal double bonds and having at least an aromatic or cycloaliphatic moiety, and said compound polymerizes with a shrinkage of less than 2.5 percent by volume and a conversion of double bonds of more than 80 percent.

5. The compound of claim 2 wherein $R_1$, $R_2$, $R_3$ and $R_4$ each independently is derived from liquid a crystalline alcohol, mercaptane, carboxylic acid, isocyanate or derivative thereof.

6. The compound of claim 2 wherein said compound has a melting point below 20° C.

7. The compound of claim 2 in a composition comprising at least one low molecular weight compound within the scope of the general formula $$Q_1-Q_2-Q_3$$

wherein $Q_1$ is a mesogenic group of the general formula

-A-Z, -A$^3$-R$^0_1$-R$^4$-Z, -A$^3$-R$^0_1$-R$^4$-R$^0_2$-R$^5$-Z or a steroidal moiety, wherein each $A^3$, $R^4$ and $R^5$ independently is a substituted or unsubstituted aromatic moiety having 6 to 24 carbon atoms, a substituted or unsubstituted heteroaromatic moiety having 2 to 24 carbon atoms or a substituted or unsubstituted cycloalkylene moiety having 5 to 30 carbon atoms each $R^0_1$ and $R^0_2$ independently is a covalent bond, OCO, N=N, CH=N, C=C, CO, O(CO)O, O, S, SO$_2$, OCS, CH$_2$—O, CH$_2$—S,

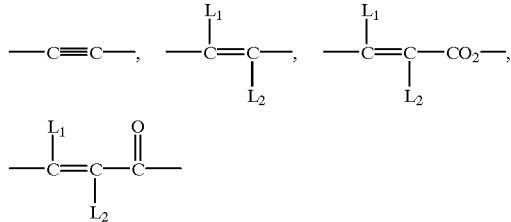

each $L_1$ and $L_2$ independently is a hydrogen, a alkyl having 1 to 20 carbon atoms or CN Z is a hydrogen, CN, —OR, COOR, NO$_2$, alkyl having 1 to 20 carbon atoms, halogen substituted or unsubstituted alkylene or alkenyl having 2 to 20 carbon atoms, a halogen substituted or unsubstituted oxyalkylene or oxyalkenyl having 1 to 20 carbon atoms, a halogen substituted or unsubstituted thioalkylene or thioalkenyl having 1 to 20 carbon atoms, a halogen substituted or unsubstituted carboxyalkylene or alkanoylenoxy having 1 to 20 carbon atoms, $Q_2$ is a covalent bond or a substituted or unsubstituted alkylene having 1 to 20 carbon atoms, oxyalkylene having 1 to 20 carbon atoms, thioalkylene having 1 to 20 carbon atoms or a carboxyalkylene having 2 to 20 carbon atoms, $Q_3$ is hydrogen, —OCH$_3$, —OH, —Cl, —Br, —COOH, —NCO, or Si(R$_3$H$_5$O)$_3$.

8. The compound of claim 2 in a composition comprising at least 25 percent by volume volatile organic solvent.

9. The compound of claim 2 in a dental cement comprising at least 20 percent by volume filler.

10. The compound of claim 2 wherein $R_1$ is an aryl having from 6 to 24 carbon atoms, a halogen substituted aryl having 6 to 24 carbon atoms or a cycloalkylene moiety having 5 to 12 carbon atoms.

11. The compound of claim 10 wherein said compound is within the general formula:

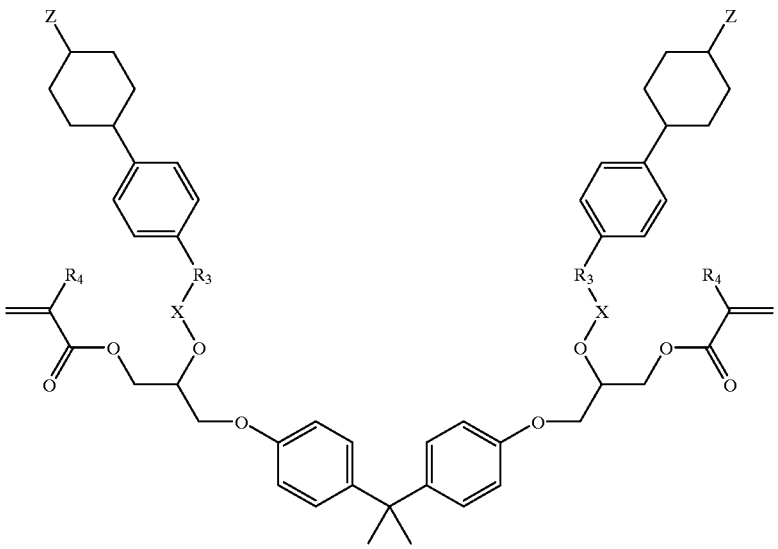

wherein
- R₃ is a covalent bond, alkylene having 1 to 20 carbon atoms, halogen substituted or unsubstituted alkylene having 2 to 20 carbon atoms, oxyalkylene having 1 to 20 carbon atoms, thioalkylene having 1 to 20 carbon atoms or a carboxyalkylene having 2 to 20 carbon atoms
- R₄ is hydrogen, halogen substituted or an unsubstituted alkyl having 1 to 20 carbon atoms, cycloalkyl having 5 to 12 carbon atoms, or aryl having 6 to 20 carbon atoms,
- Z is a hydrogen, halogen, CN, —OR, COOR, NO₂, a halogen, alkyl having 1 to 20 carbon atoms, substituted or unsubstituted alkylene or alkenyl having 2 to 20 carbon atoms, a halogen substituted or unsubstituted oxyalkylene or oxyalkenyl having 1 to 20 carbon atoms, a halogen substituted or unsubstituted thioalkylene or thioalkenyl having 1 to 20 carbon atoms, a halogen substituted or unsubstituted carboxyalkylene or alkanoylenoxy having 1 to 20 carbon atoms,
- X is a covalent bond, CO, NHCO, OCO.

12. The compound of claim 2 wherein said compound is a (meth)acrylate having a melting point below 20° C.

13. The compound of claim 2 further comprising a low molecular weight compound which is liquid at 23° C. and is within the general formula $$M\text{-}R_3\text{-}X$$

wherein
- R₃ is a covalent bond, alkylene having 1 to 20 carbon atoms, halogen substituted or unsubstituted alkylene having 2 to 20 carbon atoms, oxyalkylene having 1 to 20 carbon atoms, thioalkylene having 2 to 20 carbon atoms or a carboxyalkylene having 2 to 20 carbon atoms
- M is a mesogenic group comprising two rings and of the general formula $$\text{-}A^2\text{-}Z, \text{-}A^2\text{-}R^0{}_1\text{-}R^2\text{-}Z, \text{-}A^2\text{-}R^0{}_1\text{-}R^2\text{-}R^0{}_2\text{-}R^3\text{-}Z$$

or a steroidal moiety, wherein
- each A², R² and R³ independently is a substituted or unsubstituted aromatic moiety having 6 to 24 carbon atoms, a substituted or unsubstituted heteroaromatic moiety having 6 to 24 carbon atoms or a substituted or unsubstituted cycloalkylene moiety having 5 to 30 carbon atoms
- each $R^0{}_1$ and $R^0{}_2$ independently is a covalent bond, OCO, N=N, CH=N, C=C, CO, O(CO)O, O, S, SO₂, OCS, CH₂—O, CH₂—S,

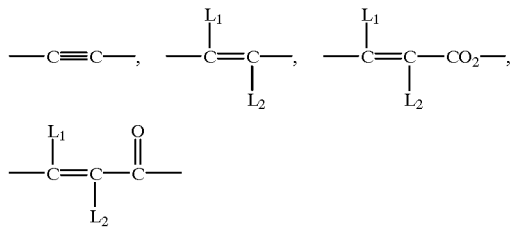

each L₁ and L₂ independently is hydrogen, alkyl having 1 to 20 carbon atoms, alkylene having 2 to 20 carbon atoms or CN Z is hydrogen, CN, —OR, COOR, NO₂, halogen, alkyl having 1 to 20 carbon atoms, halogen substituted or unsubstituted alkylene or alkylidene having 2 to 20 carbon atoms, a halogen substituted or unsubstituted oxyalkylene or oxyalkylidene having 1 to 20 carbon atoms, a halogen substituted or unsubstituted thioalkylene or thioalkylidene having 1 to 20 carbon atoms, a halogen substituted or unsubstituted carboxyalkylene or alkanoylenoxy having 2 to 20 carbon atoms.

14. A dental composition comprising a liquid crystalline compound within the scope of the general formula

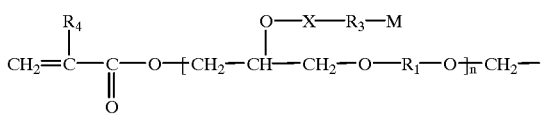

-continued

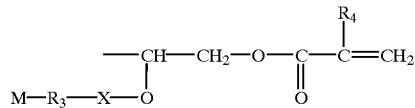

wherein

R₁ is a group of the general formula

-A'-, -A'-R⁰₁-R'-, -A'-R⁰₁-R'-R⁰₂-R"- or a steroidal moiety, wherein each $A^1$, $B^1$ and $C^1$ independently is a substituted or unsubstituted aromatic moiety having 6 to 24 carbon atoms, a substituted or unsubstituted heteroaromatic moiety having 6 to 24 carbon atoms or a substituted or unsubstituted cycloalkylene moiety having 5 to 30 carbon atoms, a substituted or unsubstituted alkylene moiety having 2 to 20 carbon atoms each $R^0_1$ and $R^0_2$ independently is a covalent bond, OCO, N=N, CH=N, C=C, CO, O(CO)O, O, S, SO₂, OCS, CH₂—O, CH₂—S,

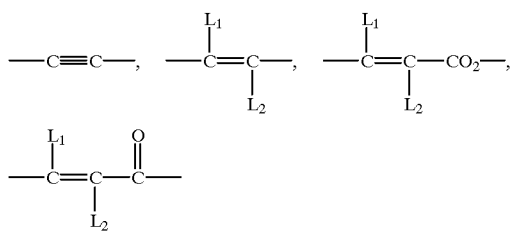

each L, and L₂ independently is hydrogen, alkyl having 1 to 20 carbon atoms, alkylene having 2 to 20 carbon atoms or CN R₃ is a covalent bond, alkyl having 1 to 20 carbon atoms, halogen substituted or unsubstituted alkylene having 2 to 20 carbon atoms, oxyalkylene having 1 to 20 carbon atoms, thioalkylene having 2 to 20 carbon atoms or a carboxyalkylene having 2 to 20 carbon atoms R₄ is hydrogen, a substituted or an unsubstituted alkyl having 1 to 20 carbon atoms, cycloalkyl having 5 to 12 carbon atoms, or aryl having 6 to 20 carbon atoms, M is a mesogenic group comprising two rings and of the general formula

-A²-Z, -A²-R⁰₁-R²-Z, -A²-R⁰₁-R²-R⁰₂-R³-Z or a steroidal moiety, wherein each $A^2$ independently is a substituted or unsubstituted aromatic moiety having up to 24 carbon atoms, a substituted or unsubstituted heteroaromatic moiety having up to 24 carbon atoms each $R^2$ and $R^3$ independently is a substituted or unsubstituted aromatic moiety having up to 24 carbon atoms, a substituted or unsubstituted heteroaromatic moiety having up to 24 carbon atoms or a substituted or unsubstituted cycloalkylene moiety having up to 30 carbon atoms each $R^0_1$ and $R^0_2$ independently is a covalent bond, OCO, N=N, CH=N, C=C, CO, O(CO)O, O, S, SO₂, OCS, CH₂—O, CH₂—S,

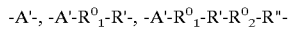

each L₁ and L₂ independently is a hydrogen, alkyl having 1 to 20 carbon atoms, alkylene having 1 to 20 carbon atoms or CN Z is hydrogen, halogen, CN, —OR, COOR, NO₂, alkyl having 1 to 20 carbon atoms, halogen substituted or unsubstituted alkylene or alkylidene having up to 20 carbon atoms, a halogen substituted or unsubstituted oxyalkylene or oxyalkylidene having up to 20 carbon atoms, a halogen substituted or unsubstituted thioalkylene or thioalkylidene having up to 20 carbon atoms, a halogen substituted or unsubstituted carboxyalkylene or alkanoylenoxy having 2 to 20 carbon atoms, X is a covalent bond, CO, NHCO, OCO n is an integer from 1 to 10, said liquid crystalline compound being in a mesomorphic state.

15. The composition of claim 14 wherein each R independently is an aryl having 6 to 24 carbon atoms, halogen substituted aryl having 6 to 24 carbon atoms or cycloalkylene moiety having 5 to 12 carbon atoms.

16. The composition of claim 14 wherein said composition comprises at least 50 percent by weight of filler particles.

17. The composition of claim 14 further comprising a polymerization initiator.

18. The composition of claim 14 further comprising a photoinitiator.

19. The composition of claim 14 wherein said composition is an adhesive, primer, cement, pit and fissure sealant or restorative.

20. A method of using a dental composition, comprising providing a dental composition comprising a liquid crystalline compound within the scope of the general formula:

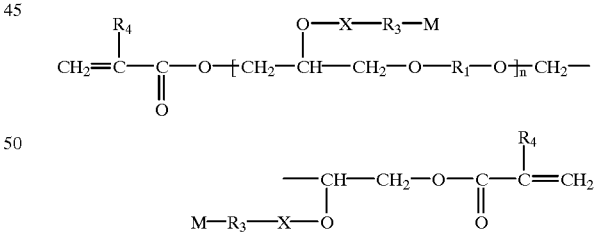

wherein

R₁ is a group of the general formula

-A'-, -A'-R⁰₁-R'-, -A'-R⁰₁-R'-R⁰₂-R"- or a steroidal moiety, wherein each A', R' and R" independently is a substituted or unsubstituted aromatic moiety having 6 to 24 carbon atoms, a substituted or unsubstituted heteroaromatic moiety having 6 to 24 carbon atoms or a substituted or unsubstituted cycloalkylene moiety having up to 30 carbon atoms, a substituted or unsubstituted alkylene moiety having up to 20 carbon atoms each $R^o_1$ and $R^o_2$ independently is a covalent bond, OCO, N=N, CH=N, C=C, CO, O(CO)O, O, S, $SO_2$, OCS, $CH_2$—O, $CH_2$—S,

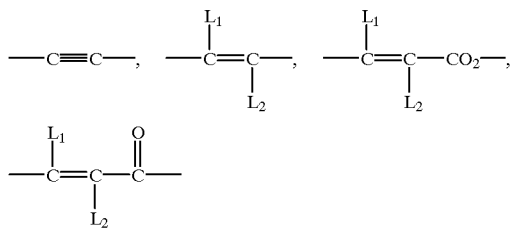

each $L_1$ and $L_2$ independently is hydrogen, alkyl having 1 to 20 carbon atoms, alkylene having 2 to 20 carbon atoms or CN $R_3$ is a covalent bond, alkyl having 1 to 20 carbon atoms, halogen substituted or unsubstituted alkylene having 2 to 20 carbon atoms, oxyalkylene having 1 to 20 carbon atoms, thioalkylene having 1 to 20 carbon atoms or a carboxyalkylene having 1 to 20 carbon atoms $R_4$ is hydrogen, a substituted or an unsubstituted alkyl having 1 to 20 carbon atoms, cycloalkyl having 5 to 12 carbon atoms, or aryl having 6 to 20 carbon atoms, M is a mesogenic group comprising two rings and of the general formula

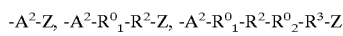

or a steroidal moiety, wherein each $A^2$ independently is a substituted or unsubstituted aromatic moiety having up to 24 carbon atoms, a substituted or unsubstituted heteroaromatic moiety having up to 24 carbon atoms each $R^2$ and $R^3$ independently is a substituted or unsubstituted aromatic moiety having up to 24 carbon atoms, a substituted or unsubstituted heteroaromatic moiety having up to 24 carbon atoms or a substituted or unsubstituted cycloalkylene moiety having up to 30 carbon atoms each $R^o_1$ and $R^o_2$ independently is a covalent bond, OCO, N=N, CH=N, C=C, CO, O(CO)O, O, S, $SO_2$, OCS, $CH_2$—O, $CH_2$—S,

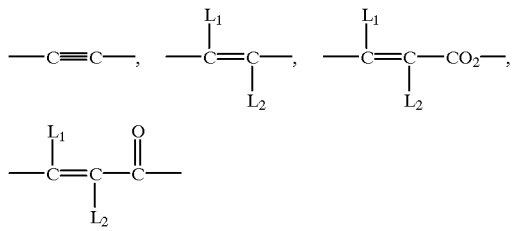

each $L_1$ and $L_2$ independently is a hydrogen, a alkylene having up to 20 carbon atoms or CN Z is a hydrogen, halogen, CN, —OR, COOR, $NO_2$, alkyl having 1 to 20 carbon atoms, halogen substituted or unsubstituted alkylene or alkenyl having 2 to 20 carbon atoms, a halogen substituted or unsubstituted oxyalkylene or oxyalkenyl having up to 20 carbon atoms, a halogen substituted or unsubstituted thioalkylene or thioalkenyl having up to 20 carbon atoms, a halogen substituted or unsubstituted carboxyalkylene or alkanoylenoxy having 2 to 20 carbon atoms, X is a covalent bond, CO, NHCO, OCO n is an integer from 1 to 10, said liquid crystalline compound being in a mesomorphic state, and polymerizing said compound to form polymeric material.

21. A method of using a dental composition, comprising providing a dental composition comprising a liquid crystalline compound within the scope of the general formula:

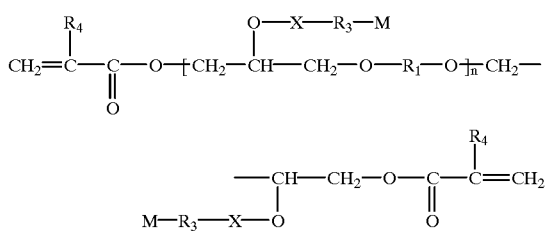

wherein $R_1$ is a group of the general formula

-A'-, -A'-$R^o_1$-R'-, -A'-$R^o_1$-R'-$R^o_2$-R"- or a steroidal moiety, selected of the group of cholesteryl compounds, wherein each A', R' and R" independently is a substituted or unsubstituted aromatic moiety having 6 to 24 carbon atoms, a substituted or unsubstituted heteroaromatic moiety having 6 to 24 carbon atoms or a substituted or unsubstituted cycloalkylene moiety having 5 to 30 carbon atoms, a substituted or unsubstituted alkylene moiety having up to 20 carbon atoms each $R^o_1$ and $R^o_2$ independently is a covalent bond, OCO, N=N, CH=N, C=C, CO, O(CO)O, O, S, $SO_2$, OCS, $CH_2$—O, $CH_2$—S,

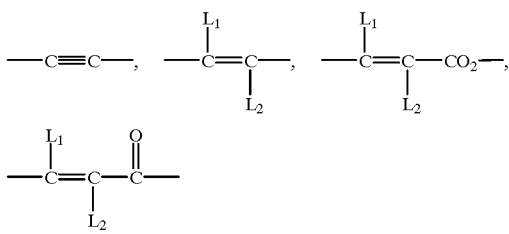

each $L_1$ and $L_2$ independently is a hydrogen, alkyl having 1 to 20 carbon atoms, alkylene having 2 to 20 carbon atoms or CN $R_3$ is a covalent bond or halogen substituted or unsubstituted alkylene having 2 to 20 carbon atoms, oxyalkylene having 1 to 20 carbon atoms, thioalkylene having 1 to 20 carbon atoms or a carboxyalkylene having 1 to 20 carbon atoms $R_4$ is hydrogen, halogen substituted or an unsubstituted alkyl having 1 to 20 carbon atoms, cycloalkyl having 5 to 12 carbon atoms, or aryl having 6 to 20 carbon atoms, M is a mesogenic group comprising two rings and of the general formula

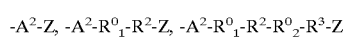

or a steroidal moiety, wherein each $A^2$ independently is a substituted or unsubstituted cycloalkylene moiety having up to 30 carbon atoms each $R^2$ independently is a substituted or unsubstituted aromatic moiety having up to 24 carbon atoms, a substituted or unsubstituted heteroaromatic moiety having up to 24 carbon atoms each $R^3$ independently is a substituted or unsubstituted aromatic moiety having up to 24 carbon atoms, a substituted or unsubstituted heteroaromatic moiety having up to 24 carbon atoms or a substituted or unsubstituted cycloalkylene moiety having up to 30 carbon atoms, a substituted or unsubstituted alkulene moiety having up to 20 carbon atoms each $R^o_1$ and $R^o_2$ independently is a covalent bond, OCO, N=N, CH=N, C=C, CO, O(CO)O, O, S, $SO_2$, OCS, $CH_2$—O, $CH_2$—S,

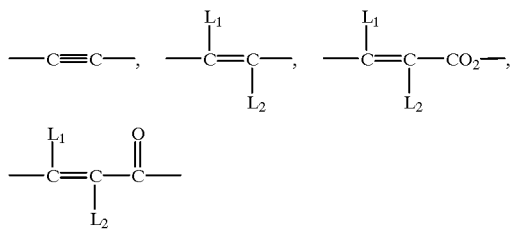

each $L_1$ and $L_2$ independently is a hydrogen, a alkylene having 1 to 20 carbon atoms or CN Z is a hydrogen, halogen, CN, —OR, COOR, $NO_2$, alkyl having 1 to 20 carbon atoms, halogen substituted or unsubstituted alkylene or alkenyl having up to 20 carbon atoms, a halogen substituted or unsubstituted oxyalkylene or oxyalkenyl having up to 20 carbon atoms, a halogen substituted or unsubstituted thioalkylene or thioalkenyl having up to 20 carbon atoms, a halogen substituted or unsubstituted carboxyalkylene or alkanoylenoxy having 2 to 20 carbon atoms, X is a covalent bond, CO, NHCO, OCO n is an integer from 1 to 10, said liquid crystalline compound being in a mesomorphic state, and polymerizing said compound.

22. The method of claims 20 or 21 wherein said composition further comprises at least 30 percent by weight of filler particles.

23. The method of claims 20 or 21 wherein said composition further comprises at least 30 percent by weight of a volatile organic solvent.

24. The compound of claim 1 wherein at least one of $R_1$ is a cholesterol derivative.

25. The method of claims 20 or 21 further comprising adhering said composition to a natural tooth.

26. The compound of claim 1 in a composition adhered to a natural tooth in a patient's mouth.

27. The method of claim 20 further comprising applying said composition to a natural tooth.

28. A liquid crystalline compound within the scope of the general formula:

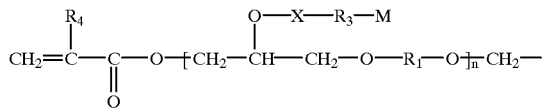

-continued

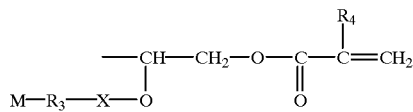

wherein $R_1$ is a group of the general formula $-R'_{10}-, -R'_{10}-Z_1-R'_{11}-, -R'_{10}-Z_1-R'_{11}-Z_2-R'_{12}-$ or a steroidal moiety, wherein each $R'_{10}$, $R'_{11}$ and $R'_{12}$ independently is a substituted or unsubstituted aromatic moiety having 6 to 24 carbon atoms, a substituted or unsubstituted heteroaromatic moiety having 6 to 24 carbon atoms each $Z_1$ and $Z_2$ independently is a covalent bond, OCO, N=N, CH=N, C=C, CO, O(CO)O, O, S, $SO_2$, OCS, $CH_2$—O, $CH_2$—S,

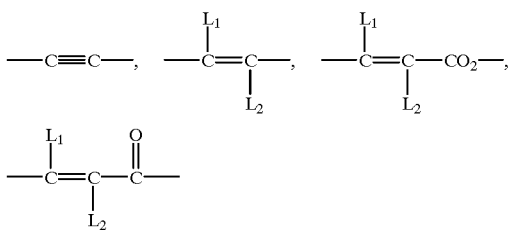

each $L_1$ and $L_2$ independently is hydrogen, alkyl having 1 to 20 carbon atoms, alkylene having 2 to 20 carbon atoms or CN $R_3$ is a covalent bond, alkyl having 1 to 20 carbon atoms, halogen substituted or unsubstituted alkylene having 2 to 20 carbon atoms, oxyalkylene having 1 to 20 carbon atoms, thioalkylene having 1 to 20 carbon atoms or a carboxyalkylene having 2 to 20 carbon atoms $R^4$ is hydrogen, a substituted or an unsubstituted alkyl having 1 to 20 carbon atoms, cycloalkyl having 5 to 12 carbon atoms, or aryl having 6 to 20 carbon atoms, M is a mesogenic group comprising two rings and of the general formula $-R'_{10}-, -R'_{10}-Z_1-R'_{11}-, -R'_{10}-Z_1-R'_{11}-Z_2-R'_{12}-Z$ or a steroidal moiety, wherein each $R'_{10}$, $R'_{11}$ and $R'_{12}$ independently is a substituted or unsubstituted aromatic moiety having 6 to 24 carbon atoms, a substituted or unsubstituted heteroaromatic moiety having 6 to 24 carbon atoms or a substituted or unsubstituted cycloalkylene moiety having 5 to 30 carbon atoms each $Z_1$ and $Z_2$ independently is a covalent bond, OCO, N=N, CH=N, C=C, CO, O(CO)O, O, S, $SO_2$, OCS, $CH_2$—O, $CH_2$—S,

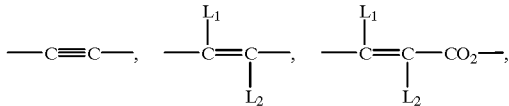

-continued

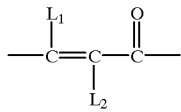

each $L_1$ and $L_2$ independently is a hydrogen, alkylene having up to 20 carbon atoms or CN Z is hydrogen, halogen, CN, —OR, COOR, $NO_2$, halogen substituted or unsubstituted alkylene or alkenyl having up to 20 carbon atoms, a halogen substituted or unsubstituted oxyalkylene or oxyalkenyl having up to 20 carbon atoms, a halogen substituted or unsubstituted thioalkylene or thioalkenyl having up to 20 carbon atoms, a halogen substituted or unsubstituted carboxyalkylene or alkanoylenoxy having 2 to 20 carbon atoms, X is a covalent bond, CO, NHCO, OCO n is an integer from 1 to 10, said liquid crystalline compound being in a mesomorphic state.

29. A liquid crystalline compound within the scope of the general formula:

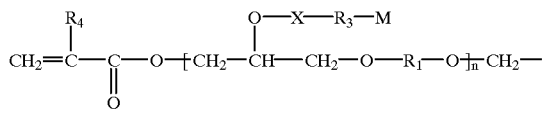

wherein $R_1$ is a group of the general formula $-R_{10}-, -R_{10}-Z_1-R_{11}-, -R_{10}-Z_1-R_{11}-Z_2-R_{12}-$ or a steroidal moiety, wherein each $R_{10}$, $R_{11}$, and $R_{12}$ independently is a substituted or unsubstituted aromatic moiety having 6 to 24 carbon atoms, a substituted or unsubstituted heteroaromatic moiety having 6 to 24 carbon atoms each $Z_1$ and $Z_2$ independently is a covalent bond, OCO, N=N, CH=N, C=C, CO, O(CO)O, O, S, $SO_2$, OCS, $CH_2$—O, $CH_2$—S,

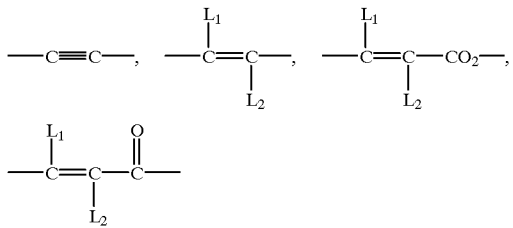

each $L_1$ and $L_2$ independently is hydrogen, alkylene having up to 20 carbon atoms or CN $R_3$ is a covalent bond or a halogen substituted or unsubstituted alkylene having up to 20 carbon atoms, oxyalkylene having up to 20 carbon atoms, thioalkylene having up to 20 carbon atoms or a carboxyalkylene having 2 to 20 carbon atoms $R_4$ is hydrogen, halogen substituted or an unsubstituted alkyl having 1 to 20 carbon atoms, cycloalkyl having 5 to 12 carbon atoms, or aryl having 6 to 20 carbon atoms, M is a mesogenic group comprising two rings and of the general formula $-R'_{10}-Z, -R'_{10}-Z_1-R'_{11}-Z, -R'_{10}-Z_1-R'_{11}-Z_2-R'_{12}-Z$ or a steroidal moiety, wherein each $R'_{10}$, $R'_{11}$ and $R'_{12}$ independently is a substituted or unsubstituted aromatic moiety having 6 to 24 carbon atoms, a substituted or unsubstituted heteroaromatic moiety having 6 to 24 carbon atoms or a substituted or unsubstituted cycloalkylene moiety having 5 to 30 carbon atoms each $Z_1$ and $Z_2$ independently is a covalent bond, OCO, N=N, CH=N, C=C, CO, O(CO)O, O, S, $SO_2$, OCS, $CH_2$—O, $CH_2$—S,

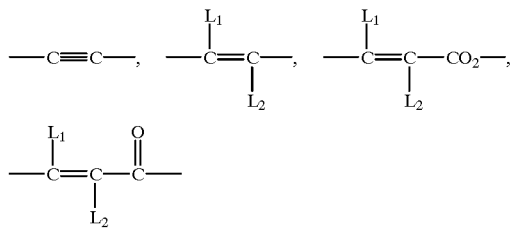

each $L_1$ and $L_2$ independently is a hydrogen, a alkylene having up to 20 carbon atoms or CN Z is a hydrogen, halogen, CN, —OR, COOR, $NO_2$, halogen substituted or unsubstituted alkylene or alkenyl having up to 20 carbon atoms, a halogen substituted or unsubstituted oxyalkylene or oxyalkenyl having up to 20 carbon atoms, a halogen substituted or unsubstituted thioalkylene or thioalkenyl having up to 20 carbon atoms, a halogen substituted or unsubstituted carboxyalkylene or alkanoylenoxy having 2 to 20 carbon atoms, X is a covalent bond, CO, NHCO, OCO n is an integer from 1 to 10, said liquid crystalline compound being in a mesomorphic state.

30. The compound of claim 29 wherein said compound is a liquid crystalline between −10 and 19° C.

31. The compound of claim 29 wherein X is a covalent bond, NHCO, or OCO and $R_3$ is a covalent bond or a alkylene, oxyalkylene or thioalkylene.

32. The dental composition of claim 14 wherein the compound is a liquid crystalline between −10 and 19° C.

33. The dental composition of claim 14 wherein X is a covalent bond, NHCO, or OCO and $R_3$ is a covalent bond or a alkylene, oxyalkylene or thioalkylene.

34. The dental composition of claim 14 wherein said compound is a liquid crystalline between −10 and 19° C.

35. The dental composition of claim 14 wherein X is a covalent bond, NHCO, or OCO and $R_3$ is a covalent bond or a alkylene, oxyalkylene or thioalkylene.

36. The dental composition of claim 20 wherein said compound is a liquid crystalline between −10 and 19° C.

37. The dental composition of claim 20 wherein X is a covalent bond, NHCO, or OCO and $R_3$ is a covalent bond or a alkylene, oxyalkylene or thioalkylene.

* * * * *